(12) United States Patent
Striedner et al.

(10) Patent No.: US 10,752,930 B2
(45) Date of Patent: *Aug. 25, 2020

(54) METHOD FOR PRODUCING A RECOMBINANT PROTEIN ON A MANUFACTURING SCALE

(71) Applicants: BOEHRINGER INGELHEIM RCV GMBH & CO KG, Vienna (AT); SANDOZ AG, Basel (CH)

(72) Inventors: Gerald Striedner, Vienna (AT); Johann Huber, Vien (AT); Daniela Reinisch, Vienna (AT)

(73) Assignees: Boehringer Ingelheim RCV GmbH & Co KG, Vienna (AT); Sandoz AG, Basel (CH)

( * ) Notice: Subject to any disclaimer, the term of this patent is extended or adjusted under 35 U.S.C. 154(b) by 55 days.

This patent is subject to a terminal disclaimer.

(21) Appl. No.: 15/594,249

(22) Filed: May 12, 2017

(65) Prior Publication Data

US 2017/0253900 A1    Sep. 7, 2017

Related U.S. Application Data

(63) Continuation of application No. 12/599,843, filed as application No. PCT/EP2008/056062 on May 16, 2008, now Pat. No. 9,683,252.

(30) Foreign Application Priority Data

May 17, 2007    (EP) .................................... 07009872

(51) Int. Cl.
    *C12P 21/02*      (2006.01)
    *C12N 15/70*      (2006.01)
    *C12N 15/90*      (2006.01)

(52) U.S. Cl.
    CPC .............. *C12P 21/02* (2013.01); *C12N 15/70* (2013.01); *C12N 15/902* (2013.01)

(58) Field of Classification Search
    None
    See application file for complete search history.

(56) References Cited

U.S. PATENT DOCUMENTS

| | | | |
|---|---|---|---|
| 4,952,496 A | 8/1990 | Studier et al. | |
| 9,683,252 B2 * | 6/2017 | Striedner | C12N 15/70 |
| 2003/0017553 A1 * | 1/2003 | Crafton | C07K 14/34 |
| | | | 435/106 |
| 2004/0235173 A1 | 11/2004 | Bleck et al. | |
| 2005/0009029 A1 | 1/2005 | Frye et al. | |
| 2005/0136049 A1 | 6/2005 | Ledbetter et al. | |
| 2006/0014146 A1 | 1/2006 | Soucaille et al. | |
| 2008/0085535 A1 * | 4/2008 | Breuner | C12N 15/1082 |
| | | | 435/69.1 |

FOREIGN PATENT DOCUMENTS

| | | |
|---|---|---|
| JP | 10-078436 A | 3/1998 |
| WO | 99/29837 A2 | 6/1999 |
| WO | 01/04288 A1 | 1/2001 |
| WO | 01/09351 A1 | 2/2001 |
| WO | 01/18222 A1 | 3/2001 |
| WO | 02/14495 A2 | 2/2002 |
| WO | 03/050240 A2 | 6/2003 |
| WO | 2004/056973 A3 | 7/2004 |
| WO | 2004/080386 A2 | 9/2004 |
| WO | 2005/097990 A1 | 10/2005 |
| WO | 2005/098002 A1 | 10/2005 |
| WO | 2006/029985 A2 | 3/2006 |
| WO | 2006/116400 A2 | 11/2006 |

OTHER PUBLICATIONS

Deboy et al. Target Site Selection by Tn7: attTn7 Transcription and Target Activity. 2000. Journal of Bacteriology. vol. 182, No. 11, pp. 3310-3313. (Year: 2000).*
Barnard et al., "High level recombinant protein expression in *Ralstonia eutropha* using T7 RNA polymerase based amplification," *Protein Expression and Purification* 38:264-271 (2004).
BitesizeBio (last viewed on Aug. 9, 2012).
Blond et al., Solution structure of microcin J25, the single macrocyclic antimicrobial peptide from *Escherichia coli.*, *European Journal of Biochemistry* 268(7):2124-2133 (2001).
Chang et al., "High-level expression of a lacZ gene from a bacterial chromosome in *Escherichia coli,*" *Appl. Microbiol. Biotechnol.* 61:234-239 (2003).
Choi et al., "A Tn7-based broad-range bacterial cloning and expression system," *Nature Methods* 2:443-448 (2005).
Datsenko et al., One-Step Inactivation of Chromosomal Genes in *Escherichia coli* K-12 Using PCR Products; *PNAS* 97(12):6640-6645 (2000).
Eun, "Enzymology Primer for Recombinant DNA Technology," *Academic Press, Inc.*, pp. 534, 535, 537 and 538 (1996).
Huber et al., "Filamentous phage integration requires the host recombinases XerC and XerD," *Nature* 417:656-659 (2002).
International Search Report and Written Opinion for PCT/EP2008/056062 dated Jul. 28, 2008.
Jain, "Overexpression and Purification of Tagged *Escherichia coli* Proteins Using a Chromosomal Knock-in Strategy," *Protein Expression and Purification* 46(6):294-298 (2006).
Jeong et al., "High-Level Production of Human Leptin by Fed-Batch Cultivation of Recombinant *Escherichia coli* and its Purification," *Appl Environ Microbiol.* 65(7):3027-3032 (Jul. 1999).
Lee et al., "Optimal Fed-Batch Control of Induced Foreign Protein Production by Recombinant Bacteria," *AIChE Journal* 40:899-907 (1994).
Lee et al., "Sequential δ-Integration for the Regulated Insertion of Cloned Genes in *Saccharomyces cerevisiae,*" *Biotechnol. Prog.* 13:368-373 (1997).

(Continued)

*Primary Examiner* — Channing S Mahatan
(74) *Attorney, Agent, or Firm* — Seed IP Law Group LLP

(57) ABSTRACT

A method for producing a protein of interest on a manufacturing scale is based on integration, by homologous recombination, of the DNA encoding the protein of interest into a bacterial cell's genome at a pre-selected site. The manufacturing scale production of recombinant proteins is in the fed-batch mode, semi-continuous or in a chemostat.

36 Claims, 17 Drawing Sheets

(56) References Cited

OTHER PUBLICATIONS

Martinez-Morales et al., "Chromosomal Integration of Heterologous DNA in *Escherichia coli* with Precise Removal of Markers and Replicons Used During Construction," *Journal of Bacteriology* 181(22):7143-7148 (1999).

McKown et al., "Sequence requirements of *Escherichia coli* attTn7, a specific site of transposon Tn7 insertion," *J Bacteriol.* 170(1):352-358 (1988).

Merriam-Webster definition of genome (last viewed on Aug. 9, 2012).

Murphy, "Use of Bacteriophage λ Recombination Functions to Promote Gene Replacement in *Escherichia coli*," *Journal of Bacteriology* 180(8):2063-2071 (1998).

Muyrers et al., "Et-Cloning: Think Recombination First," *Genetic Engineering* 22:77-98 (2000).

Muyrers et al., "Techniques, Recombinogenic Engineering—New Options for Cloning and Manipulation DNA," *Trends in Biochemical Sciences* 26(5):325-331 (2001).

Olson et al., "High Level Expression of Eukaryotic Polypeptides from Bacterial Chromosomes," *Protein Expression and Purification* 14:160-166 (1998).

Panda et al., "Kinetics of inclusion body production in batch and high cell density fed-batch culture of *Escherichia coli* expressing ovine growth hormone," *Journal of Biotechnology* 75(2-3):161-172 (Oct. 8, 1999).

pET21a-d (last viewed on Aug. 9, 2012).

Phenylalanine (last viewed on Aug. 9, 2012).

Rai et al., "Expression systems for production of heterologous proteins," *Current Science* 80:1121-1128 (2001).

Rogers et al., "Analysis of tn7 transposition," *Mol Gen Genet* 205:550-556 (1986).

Salleh et al., "New Lipases and Proteases," Nova Science Publishers, Inc., New York, pp. 41-58 (2006).

Srinivasan et al., "Production of Recombinant Proteins Using Multiple-Copy Gene Integration in High-Cell-Density Fermentations of *Ralstonia eutropha*," *Biotechnology and Bioengineering* 84(1):114-120 (2003).

Waddell et al., "Tn7 transposition: recognition of the attTn7 target sequence," *Proc. Natl. Acad. Sci. USA* 86:3958-3962 (1989).

Whitney et al., "Induction of T4 DNA Ligase in a Recombinant Strain of *Escherichia coli*," *Biotechnology and Bioengineering* 33:991-998 (1989).

Wink, "An Introduction to Molecular Biotechnology," Molecular Fundamental, Methods and Applications in Modern Biotechnology, Wiley-VCHVerlag GmbH & Co. KGaA, pp. 211-212 (2006).

\* cited by examiner

METHOD FOR PRODUCING A RECOMBINANT PROTEIN ON A MANUFACTURING SCALE

CROSS REFERENCE TO RELATED APPLICATIONS

The present application is a continuation application of U.S. application Ser. No. 12/599,843 filed Aug. 11, 2010, now pending, which is a U.S. national phase application of PCT/EP08/56062 filed May 16, 2008, which claims priority to EP Application No. 07009872.8 filed May 17, 2007. U.S. application Ser. No. 12/599,843 is herein incorporated by reference in its entity.

BACKGROUND

The present invention relates to the production of recombinant proteins in bacterial host cells on a manufacturing scale.

Currently, production of recombinant proteins in bacterial hosts, in particular *Escherichia coli*, mostly uses plasmid-based expression systems. Since these systems provide high gene dosage and are well established, they have become widely accepted, also because the available cloning protocols are simple to handle.

Plasmid-based expression is characterized by plasmid copy numbers up to several hundred per cell (Baneyx, 1999). Expression plasmids usually carry the gene of interest under the control of a promoter, an origin of replication (ori) and a marker gene for selection of plasmid-carrying clones. In addition, coding or non-coding or non-functional backbone sequences are frequently present on said plasmids (i.e. vectors). The presence of plasmids and the corresponding replication mechanism alter the metabolism of the host cell (Diaz-Rizzi and Hernandez, 2000) and impose a high metabolic burden on the cells, thereby limiting their resources for recombinant protein production. In addition, the application of strong promoters in combination with high gene dosage triggers a rate of recombinant protein formation that is usually too high for the host cell to cope with and may therefore lead to a quick and irreversible breakdown of the cell metabolism. Consequently, the host cell's potential cannot be fully exploited in plasmid-based systems, resulting in low yield and quality of the recombinant protein. Thus, one of the major drawbacks of plasmid-based expression systems may be attributed to the increased demand for nutrients and energy that is required for plasmid replication and maintenance.

Another typical phenomenon in plasmid-based systems is the change of plasmid copy number in the course of cultivation. Recombinant protein production is accompanied, at high expression rates, with starvation and cellular stress that lead to increased pools of uncharged tRNAs. This leads to an interference with the control mechanism of plasmid copy number (PCN). Consequently, PCN increases rapidly and causes a breakdown of the cultivation process (so-called "run-away effect"). The run-away phenomenon of ColE1 type plasmids after induction of recombinant gene expression can lead to a strong increase of gene dosage (Grabherr et al., 2002).

Segregational instability, (i.e. the formation of plasmid free host cells) and structural instability (i.e. mutations in plasmid sequence) are further problems often seen in plasmid-based systems. During cell division, cells may lose the plasmid and, consequently, also the gene of interest. Such loss of plasmid depends on several external factors and increases with the number of cell divisions (generations). This means that plasmid-based fermentations are limited with regard to the number of generations or cell doublings (Summers, 1991).

Overall, due to these properties of plasmid-based expression systems, there is a limited yield of recombinant protein and a reduced controllability of process operation and process economics. Nevertheless, due to lack of more efficient alternatives, plasmid-based bacterial expression systems became state of the art for production and isolation of heterologous recombinant proteins on a manufacturing scale.

Therefore, as an alternative to plasmid-based expression, genome-based expression systems have been explored. A well-known and widely-applied example for a heterologous protein that is chromosomally expressed in *E. coli*, is the RNA polymerase of the T7 phage, which serves the purpose of plasmid-based transcription of a plasmid-based gene of interest. This system, which is originally described in U.S. Pat. No. 4,952,496, is based on non-site specific integration, and renders the resulting bacterial strains (e.g. *E. coli* BL21(DE3) or HMS174(DE3)) as lysogens. To prevent potential cell lysis followed by undesired phage release, the T7 polymerase gene was integrated into the chromosome without creating phage lysogen, i.e. it was inserted by homologous recombination (WO 2003/050240). Recently, integration of T7 RNA polymerase gene into the genome of *Corynebacterium acetoacidophilum* has been described, again for the purpose of plasmid-based expression of recombinant proteins (US 2006/0003404).

Other methods for genomic integration of nucleic acid sequences—in which recombination is mediated by the Red recombinase function of the phage λ (Murphy, 1998) or the RecE/RecT recombinase function of the Rac prophage (Zhang et al., 1998)—have been suggested for protein expression studies, sequence insertions (e.g. of restriction sites, site-specific recombinase target sites, protein tags, functional genes, promoters), deletions and substitutions (Muyrers et al., 2000).

WO 2001/18222 describes utilization of a chromosomal integration method based on the *Saccharomyces cerevisiae* FLP (flippase)/FRT (flippase recognition target) recombination system (Pósfai et al., 1994) for insertion of ethanol pathway genes from *Zymomonas mobilis* downstream of chromosomal promoters of *E. coli* in order to confer ethanologenic properties to that host. The FLP system was used for precisely removing sequences (markers and replicons) after chromosomal integration of circular vectors (Martinez-Morales et al., 1999).

A method developed by Datsenko and Wanner (2000) for insertion of linear DNA fragments with short homology sequences, utilizing the λ Red technology in combination with the FLP-based marker excision strategy, has been applied for the insertion of an antibiotic resistance gene for chromosomal gene replacement (Murphy, 1998) or for gene disruption (Datsenko and Wanner, 2000). Also, this method has been suggested for overexpression of tagged homologous *E. coli* proteins by the chromosomal insertion of a marker, a promoter and a His-tag prior to (i.e. upstream of) said proteins (Jain, 2005).

Genome-based expression was also suggested for integration of a repressor molecule into the chromosome of *E. coli* to establish a host/vector selection system for propagation of plasmids without an antibiotic resistance marker (WO 2006/029985). In the context of that selection system, the genomic insertion of a reporter protein (green fluorescent protein) was used as a model system to demonstrate a plasmid-derived RNAI/II antisense reaction (Pfaffenzeller et al., 2006). In a similar way, Zhou et al., (2004) described the integration of a circular vector carrying green fluorescent protein as a reporter molecule.

In WO 1996/40722, a method is described that makes use of integration of a circular vector (so-called "circular chromosomal transfer DNA", CTD) including a selectable marker into the bacterial chromosome (i.e. at the attB site of *E. coli*). In that method, by using duplicate DNA sequences flanking the selection marker, amplification of the chromosomal gene dosage was achieved. Thereby, the obtained chromosomal gene dosage was approximately 15-40 copies per cell, which is similar to those achieved by commonly used plasmid vectors. Cultivation of clones containing chromosomal transfer DNA integrated into the bacterial genome resulted in levels of recombinant proteins similar to those obtained by plasmid-based systems (Olson et al., 1998). This method requires in vitro ligation of CTD and is, with regard to integration, limited to the attB site.

BRIEF SUMMARY

It was an object of the invention to provide a novel manufacturing scale expression method for producing recombinant proteins.

The present invention relates to a method for producing a recombinant protein of interest on a manufacturing scale, comprising the steps of
a) cultivating a population of bacterial expression host cells,
b) harvesting the protein of interest, and
c) isolating and purifying it, wherein
in step a), cultivation is in a mode that employs the addition of a feed medium, said mode being selected from the fed-batch, semi-continuous or continuous mode, and wherein said bacterial expression host cells contain, integrated in their genome, a DNA construct carrying the DNA sequence encoding the protein of interest under the control of a promoter that enables expression of said protein.

In the following, the term "host cell" designates the bacterial cell that is used as the starting cell prior to its transformation with the DNA construct carrying the gene of interest. The cell that has, upon transformation, the linear DNA construct that carries the gene of interest, integrated in its genome, is termed "expression host cell".

The expression cassette contains, as its essential elements, the gene of interest, a promoter and a ribosome binding site (RBS). Additionally, the expression cassette may contain sequences encoding "helper proteins", e.g. markers or proteins that favour growth of the expression host cell, e.g. genes relevant for sugar or protein metabolism and/or proteins that improve expression of the gene of interest, e.g. chaperon molecules (like GroE1 or GroEs) or genes that are involved in transcription and translation.

DETAILED DESCRIPTION

Protein of Interest

With regard to the protein of interest, there are no limitations. It may, in principal, be any protein that is to be produced on a manufacturing scale, e.g. an industrial protein or a therapeutic protein. Examples for proteins that can be produced by the method of the invention are, without limitation, enzymes, regulatory proteins, receptors, peptides, e.g. peptide hormones, cytokines, membrane or transport proteins. The proteins of interest may also be antigens as used for vaccination, vaccines, antigen-binding proteins, immune stimulatory proteins, allergens, full-length antibodies or antibody fragments or derivatives. Antibody derivatives may be selected from the group of single chain antibodies, (scF$_V$), Fab fragments, F$_V$ fragments, single domain antibodies (V$_H$ or V$_L$ fragment), domain antibodies like camelid single domain antibodies (V$_{HH}$, nanobodies) or other antibody formats as described for instance in Andersen and Reilly (2004) or Holliger and Hudson (2005). The DNA molecule encoding the protein of interest is also termed "gene of interest".

Promoter

"Promoter" in the meaning of the present invention is an expression control element that permits binding of RNA polymerase and the initiation of transcription. In one embodiment of the invention, the gene of interest is under the control of a "strong" promoter. A strong promoter is characterized by a high binding affinity of the promoter sequence to an RNA polymerase, usually the naturally occurring corresponding RNA polymerase, on the one hand and the rate of formation of mRNA by that RNA polymerase on the other hand.

Preferably, the gene of interest is under the control of an inducible promoter. An inducible promoter is a promoter that is regulable by external factors, e.g. the presence of an inductor (also termed "inducer") molecule or the absence of a repressor molecule, or physical factors like increased or decreased temperature, osmolarity, or pH value. Different promoters and the respective induction principles were reviewed by Makrides (1996).

In the present invention, promoters may be used that have been developed for plasmid-based expression, among the strong promoters, the T7 promoter of bacteriophage T7 has been most widely used.

In a preferred aspect, the promoter is the T7 promoter. T7-based expression systems, comprising a combination of the T7 promoter and T7 polymerase gene under the control of the lac promoter, are widely used for large scale expression of recombinant proteins in both bacterial and eukaryotic cells. The system makes use of the T7 RNA polymerase, transcription rate of which is several times higher than *E. coli* RNA polymerase. The expression from the T7 promoter is under the control of T7 RNA polymerase, which is stringently specific for the T7 promoter (Chamberlin et al., 1970), i.e. the T7 promoter can only be utilized by the polymerase of bacteriophage T7. When IPTG is added to the culture medium, T7 RNA polymerase is expressed by transcription from the lac promoter.

In the meaning of the present invention, the term "T7 promoter" includes promoters that are present in the genome of bacteriophage T7, as well as consensus sequences and variants of such promoters with the ability to mediate transcription by the T7 RNA polymerase. The bacteriophage T7 contains seventeen different promoter sequences, all of which comprise a highly conserved nucleotide sequence (Oakley and Coleman, 1977; Panayotatos and Wells, 1979).

According to certain embodiments of the invention, the gene of interest may be under the control of the tac or the trc promoter, the lac or the lacUV5 promoter (all inducible by lactose or its analogue IPTG (isopropylthiol-β-D-galactoside)), the tightly regulatable araBAD promoter (P$_{BAD}$, Guzman et al., 1995, inducible by arabinose), the trp promoter (inducible by β-indole acrylic acid addition or tryptophan starvation, repressible by tryptophan addition), the lambda promoter pL (λ) (induction by an increase of temperature), the phoA promoter (inducible by phosphate starvation) or other promoters suitable for recombinant protein expression (Makrides, 1996), which all use *E. coli* RNA polymerase.

Among inducible promoters are those that show a "leaky" expression behaviour. Such promoters (so-called "leaky promoters") are, in principle, inducible, but show nevertheless also basal expression without being externally induced. Inducible promoters that show leaky expression under non-induced conditions may behave similarly to constitutive promoters (i.e. they are steadily and continuously active or they may be activated or enhanced as a result of certain cultivation conditions). Leaky promoters may be particularly useful for continuously operated cultivation processes. Examples are the T7 promoter and the trp promoter.

In the method of the invention, the promoter may also be constitutive, i.e. a promoter which controls expression without the need for induction on the one hand, or the possibility of repression on the other hand. Hence, there is continuous and steady expression at a certain level. Aside the advantage that they do not require an inducer, constitutive promoters are particularly useful in embodiments where the method is continuous (as described below). As an example, the strong constitutive HCD promoter (Poo et al., 2002; Jeong et al., 2004) may be applied for constitutive expression.

The linear cassette integrated in the genome of the bacterial cells also contains, immediately upstream of the gene of interest, a Shine-Dalgarno (SD) sequence, also termed ribosome binding site (RBS).

Expression Cartridge

In the following, the linear or circular DNA construct to be integrated into the bacterial genome is also termed "expression cartridge" or "cartridge". As a result of integration, the expression host cell has an integrated "expression cassette". Preferably, the cartridge is a linear DNA construct comprising essentially a promoter, a gene of interest, a ribosome binding site and two terminally flanking regions which are homologous to a genomic region and which enable homologous recombination (see insertion cartridge shown in FIG. 10). In addition, the cartridge may contain other sequences as described below in detail; e.g. sequences coding for antibiotic selection markers, prototrophic selection markers or fluorescent markers, markers coding for a metabolic gene, genes which improve protein expression (like e.g. the T7 RNA polymerase gene) or two flippase recognition target sites (FRT) which enable the removal of certain sequences (e.g. antibiotic resistance genes) after integration.

The cartridge is synthesized and amplified by methods known in the art, in the case of linear cartridges, usually by standard polymerase chain reaction, PCR (Wilson and Walker, 2005). Since linear cartridges are usually easier to construct, they are preferred for obtaining the expression host cells used in the method of the invention. Moreover, the use of a linear expression cartridge provides the advantage that the genomic integration site can be freely chosen by the respective design of the flanking homologous regions of the cartridge. Thereby, integration of the linear expression cartridge allows for greater variability with regard to the genomic region.

Host Cells

Regarding the bacterial host cells, there are, in principle, no limitations; they may be eubacteria (gram-positive or gram-negative) or archaebacteria, as long as they allow genetic manipulation for insertion of a gene of interest, advantageously for site-specific integration, and can be cultivated on a manufacturing scale. Preferably, the host cell has the property to allow cultivation to high cell densities.

Examples for bacterial host cells that have been shown to be suitable for recombinant industrial protein production are *Escherichia coli* (Lee, 1996; Hannig and Makrides, 1998), *Bacillus subtilis, Pseudomonas fluorescens* (Squires et al., 2004; Retallack et al., 2006) as well as various *Corynebacterium* (US 2006/0003404 A1) and *Lactococcus lactis* (Mierau et al., 2005) strains. Preferably, the host cells are *E. coli* cells.

Another requirement to the host cell is that it contains an RNA polymerase that can bind to the promoter controlling the gene of interest. The RNA polymerase may be endogenous or foreign to the host cell.

Preferably, host cells with a foreign strong RNA polymerase are used. Most preferably host strains, e.g. *E. coli* strains, are used that have been engineered to carry a foreign RNA polymerase (like e.g. in the case of using a T7 promoter a T7-like RNA polymerase in the so-called "T7 strains") integrated in their genome. Examples for T7 strains are widely used and commercially available, e.g. BL21 (DE3), HMS174(DE3) and their derivatives or relatives (Novagen, pET System manual, $11^{th}$ edition). These strains are DE3 lysogens containing the T7 RNA polymerase gene under control of the lacUV5 promoter. Induction with IPTG allows production of T7 RNA polymerase which then directs the expression of the gene of interest under the control of the T7 promoter.

Preferably, a host cell is used that contains a T7 RNA polymerase which has been genome-integrated without generating phage lysogens, e.g. as described in WO 2003/050240. (Cells that do not generate phage lysogens are "non-lysogenic").

A "T7-like RNA polymerase" includes, but is not limited to, RNA polymerases from other T7-like phages, such as the T3 RNA polymerase, as disclosed in U.S. Pat. No. 4,952, 496. A prerequisite of a T7-like RNA polymerase is that there should be a highly specific cognate promoter, and that the gene of interest is transcribed at a high rate in the presence of said RNA polymerase.

Alternatively to using the above-mentioned strains carrying the T7 RNA polymerase, such strains can be generated de novo, e.g. as described in U.S. Pat. No. 4,952,496, US 2006/0003404, or WO 2003/050240.

The host cell strains *E. coli* BL21(DE3) or HMS174 (DE3), which have received their genome-based T7 RNA polymerase via the phage DE3, are lysogenic. Lysogenic strains have the disadvantage to potentially exhibit lytic properties, leading to undesirable phage release and cell lysis. For the invention, it is therefore preferred that the T7 RNA polymerase contained in the host cell has been integrated by a method which avoids, or preferably excludes, the insertion of residual phage sequences in the host cell genome. In a preferred embodiment of the invention, the host cell has been obtained by integrating the T7 polymerase into the cell's genome by site-directed integration, e.g. according to the method described by Datsenko and Wanner (2000).

In the case of using the T7 system, a host cell may be used that has the T7 RNA polymerase in combination with its promoter (preferably the lacUV5 promoter) integrated in its genome.

Alternatively, the T7 RNA polymerase may be provided as an element of the expression cartridge and thus becomes integrated into the cell's genome as part of the expression cassette.

Another requirement to the host cell is its ability to carry out homologous recombination (which is relevant for integration of the expression cartridge into the genome and optionally for P1 transduction).

Therefore, the host cell preferably carries the function of the recombination protein RecA. However, since RecA may cause undesirable recombination events during cultivation, the host cell preferably has a genomic mutation in its genomic recA site (rendering it dysfunctional), but has instead the RecA function provided by a recA sequence present on a helper plasmid, which can be removed (cured) after recombination by utilizing the helper plasmid's temperature-sensitive replicon (Datsenko and Wanner, 2000).

In view of recombination, in addition to RecA, the host cell preferably contains, in its genome, DNA sequences encoding recombination proteins (e.g. Exo, Beta and Gam). In this case, a host cell may be selected that already has this feature, or a host cell is generated de novo by genetic engineering to insert these sequences.

In view of site-specific gene insertion, another requirement to the host cell is that it contains at least one genomic region (either a coding or any non-coding functional or non-functional region or a region with unknown function) that is known by its sequence and that can be disrupted or otherwise manipulated to allow insertion of a heterologous sequence, without being detrimental to the cell.

In certain embodiments, the host cell carries, in its genome, a marker gene in view of selection.

Integration Locus

With regard to the integration locus, the expression system used in the invention allows for a wide variability. In principle, any locus with known sequence may be chosen, with the proviso that the function of the sequence is either dispensable or, if essential, can be complemented (as e.g. in the case of an auxotrophy).

When choosing the integration locus, it needs to be considered that the mutation frequency of DNA caused by the so-called "adaptive evolution" (Herring et al, 2006) varies across the genome of *E. coli* and that the metabolic load triggered by chromosomally encoded recombinant gene expression may cause an enhanced mutation frequency at the integration site. In order to obtain an expression host cell that is robust and stable, a highly conserved genomic region that results in a lowered mutation frequency is preferably selected as integration site. Such highly conserved regions of the *E. coli* genome are for instance the genes encoding components of the ribosome or genes involved in peptidoglycan biosynthesis (Mau et al., 2006), and those regions are preferably selected for integration of the expression cartridge. The exact integration locus is thereby selected in such a way that functional genes are neither destroyed nor impaired, and the integration site should rather be located in non-functional regions.

The genomic region with known sequence that can be chosen for integration of the cartridge may be selected from the coding region of a non-essential gene or a part thereof; from a dispensable non-coding functional region (i.e. promoter, transposon, etc.), from genes the deletion of which may have advantageous effects in view of production of a specific protein of interest, e.g. certain proteases, outer membrane proteins like OmpT, potential contaminants of the product, genes encoding proteins of metabolism (e.g. relevant for the metabolism of a sugar molecule that is undesirable or dispensable for a given host strain and/or fermentation process) or stress signalling pathways, e.g. those occurring in stringent response, a translational control mechanism of prokaryotes that represses tRNA and rRNA synthesis during amino acid starvation (Cashel, 1969).

Alternatively, the site of integration may be a marker gene which allows selection for disappearance of said marker phenotype after integration. Preferably, a fluorescent marker like the green fluorescent protein, the deletion of which leads to a disappearance of fluorescence, and which allows visual detection of clones that carry the expression cassette, is used (FIG. 10).

Alternatively, the site useful to select for integration is a function which, when deleted, provides an auxotrophy. In this case, the integration site may an enzyme involved in biosynthesis or metabolic pathways, the deletion of such enzyme resulting in an auxotrophic strain. Positive clones, i.e. those carrying the expression cassette, may be selected for auxotrophy for the substrate or precursor molecules of said enzymes (FIG. 10).

Alternatively, the site of integration may be an auxotrophic marker (a non-functional, i.e. defective gene) which is replaced/complemented by the corresponding prototrophic marker (i.e. a sequence that complements or replaces the defective sequence) present on the expression cassette, thus allowing for prototrophic selection.

In one aspect, the region is a non-essential gene. According to one aspect, this may be a gene that is per se non-essential for the cell.

Non-essential bacterial genes are known from the literature, e.g. from Gerdes et al. (2002 and 2003), from the PEC (Profiling the *E. coli* Chromosome) database or from the so-called "Keio collection" (Baba et al., 2006).

An example for a non-essential gene is RecA. Integrating the expression cassette at this site provides the genomic mutation described above in the context with the requirements on the host cells.

Suitable integration sites, e.g. sites that are easily accessible and/or are expected to yield higher expression rates, can be determined in preliminary screens. Such screens can be performed by generating a series of single mutant deletions according to the Keio collection (Baba et al., 2006) whereby the integration cartridge features, as variable elements, various recombination sequences that have been pre-selected in view of specific integration sites, and, as constant elements, the basic sequences for integration and selection, including, as a surrogate "gene of interest", a DNA sequence encoding an easily detectable protein under the control of an inducible promoter, e.g. the cartridge used in Example 5, encoding the Green Fluorescent Protein. The expression level of the thus created single knockout mutants can be easily quantified by fluorescence measurement. Based on the results of this procedure, a customized expression level of a desired target protein can be achieved by variation of the integration site and/or number of integrated cartridges.

In the embodiments in which the host cell contains DNA sequences encoding recombination proteins (e.g. Exo, Beta and Gam) in its genome—either as a feature of the starting cell or obtained by genetic engineering—integration can occur at the genomic site where these recombination protein sequences are located. By integration of the expression cartridge, the sequences coding for the recombination proteins are destroyed or removed and consequently need not, as in the case of plasmid-encoded helper proteins, be removed in a separate step (FIG. 9).

Integration Methods

With regard to the integration locus, as described above, any locus with known sequence may be chosen, with the proviso that the function of the sequence is either dispensable or, if essential, can be complemented. In a preferred embodiment, integration of a linear cartridge is at an attachment site like the attB site or the attTn7 site, which are well-proven integration sites. However, the flexibility of the system allows the insertion of the gene of interest at any pre-selected locus, as described above.

Integration of the gene of interest into the bacterial genome can be achieved by conventional methods, e.g. by using linear cartridges that contain flanking sequences homologous to a specific site on the chromosome, as described for the attTn7-site (Rogers et al., 1986; Waddell and Craig, 1988; Craig, 1989). The cartridge is transformed into the cells of an *E. coli* strain, e.g. *E. coli* MG1655, that contains the plasmid pKD46 (Datsenko and Wanner; 2000). This plasmid carries the phage λ derived Red function (γ☐☐β☐ exo) that promotes recombination in vivo.

Alternatively, an expression cassette can first be integrated into the genome of an intermediate donor host cell, from which it can then be transferred to the host cell by transduction by the P1 phage (Sternberg and Hoess, 1983; and Lennox, 1955), the donor cell being e.g. MG1655 or DY378 (Yu et al., 2000), an *E. coli* K12 strain which carries the defective λ prophage. In brief, P1 transduction is a method used to move selectable genetic markers from one "donor" strain to another "recipient" strain. During the replication and lysis of the phage in a culture of bacteria, a small percentage of the phage particles will contain a genome segment that contains the expression cassette. Once a phage population has been generated from a donor cell, the phage are used to infect the recipient cell, in the case of the invention, the host cell. Most of the bacteria are lysed by phage that packaged P1 genomes, but a fraction of the phage inject a genome segment derived from the donor host. Homologous recombination then allows the incoming genomic segment to replace the existing homologous segment. The infected recipient bacteria are plated on a medium that selects for the genome segment of the donor bacteria (antibiotic resistance, prototrophy, fluorescence marker, etc.). Importantly, the infectivity of the phage has to be controlled. Otherwise, phage released from neighboring cells would infect and lyse the bacteria that had been infected with transducing particles. Phage P1 requires calcium for infectivity, therefore it can be controlled by growing in the presence and absence of calcium. The calcium chelator citrate is usually used because it lowers the concentration of free calcium (by forming Ca-citrate) low enough to prevent P1 infection, but not so low as to starve the cells for calcium.

To simplify the integration procedure, as shown in FIG. 9, instead of providing the recombination proteins by means of the plasmid pKD20 or pKD46 according to Datsenko and Wanner (2000), the genes encoding the recombination functions exo, beta and gam may already be present in the chromosome of the host cell, the expression of recombination proteins being controllable by inducible promoters, e.g. frt, lac, tac, T7 or the araP promoter. By application of the corresponding inducer, the thus modified strain can be used for integration of the linear expression cartridge at the site of the recombination proteins. Thereby, the recombination proteins are first expressed and then utilized to integrate an expression cartridge into the genomic region coding for said recombination proteins. Thereby, as a consequence of recombination, and as a particular advantage of this embodiment, the genes coding for the recombination proteins are removed (excised) or destroyed (FIG. 9). Furthermore, this embodiment has the advantage that there is no need for plasmids encoding these recombination functions.

Examples, without limitation, of other integration methods useful in the present invention are e.g. those based on Red/ET recombination (Muyrers et al., 2002; Wenzel et al., 2005; Vetcher et al., 2005).

Selection Markers

Positive clones, i.e. clones that carry the expression cassette, can be selected by means of a marker gene.

In some embodiments, host cells are used that already contain a marker gene integrated in their genome, e.g. an antibiotic resistance gene or a gene encoding a fluorescent protein, e.g. GFP (as shown in FIG. 10). In this case, the expression cartridge which does not contain a selection marker, is integrated at the locus of the chromosomal marker gene, and positive clones are selected for loss/disappearance of the respective phenotype, e.g. they are selected for antibiotic sensitivity or disappearance of fluorescence, which can be directly visualized on the cultivation plates. These embodiments have the advantage that the marker is either interrupted or completely replaced by the expression cassette, and thus no functional marker sequence is present after integration and does not need to be removed, if undesirable, as in the case of antibiotic resistance genes.

Alternatively, the marker gene is part of the expression cartridge. In the case that the marker used for selection is a gene conferring antibiotic resistance (e.g. for kanamycin or chloramphenicol), positive clones are selected for antibiotic resistance (i.e. growth in the presence of the respective antibiotic), as shown in FIG. 7. Preferably, kanamycin is used for antibiotic clone selection.

The marker gene (irrespective of whether it is present on the host cell's genome or has been introduced by means of the expression cartridge) can be eliminated upon integration of the cassette, as schematically shown in FIG. 7, e.g. by using the FLP recombinase function based on the site-specific recombination system of the yeast 2 micron plasmid, the FLP recombinase and its recombination target sites FRTs (Datsenko and Wanner, 2000).

In certain embodiments, the expression cell has been engineered to carry a defective selectable marker gene, e.g. an antibiotic resistance gene like chloramphenicol or kanamycin, a fluorescent marker or a gene involved in a metabolic pathway of a sugar or an amino acid. In this case, the cartridge with the gene of interest carries the missing part of the marker gene, and by integration the marker gene restores its functionality. By way of example, the cartridge carries the missing part of the marker gene at one of its ends, and is integrated directly adjacent to the defective marker gene integrated in the genome, such that the fusion of the two fragments renders the marker gene complete and allows its functional expression. In the case of an antibiotic resistance gene, the cells carrying the expression cassette are resistant against the specific antibiotic, in the case of a fluorescent marker cells can be visualized by fluorescence, and in the case of a metabolic pathway gene, cells obtain the ability to metabolize the respective component (schematically shown in FIG. 11). The advantage of this embodiment is that only a short proportion of the marker gene of the cartridge needs to be synthesized, enabling shorter or smaller insertion cartridges compared to prior art.

In certain embodiments, selection of positive clones (i.e. clones that carry the expression cassette) is carried out by correction (i.e. complementation) of an auxotrophy of the host cell. In such embodiments, as schematically shown in FIG. 8, a host cell is used that has a mutation that has been chosen to allow selection of positive transformant colonies in an easy way, e.g. a strain that has a deletion or mutation that renders it unable to synthesize a compound that is essential for its growth (such mutation being termed as "auxotrophic marker"). For example, a bacterial mutant in which a gene of the proline synthesis pathway is inactivated, is a proline auxotroph. Such a strain is unable to synthesize proline and will therefore only be able to grow if proline can be taken up from the environment, as opposed to a proline prototroph which can grow in the absence of proline.

Any host cell having an auxotrophic marker may be used. Preferably, mutations in genes required for amino acid synthesis are used as auxotrophic markers, for instance mutations in genes relevant for the synthesis of proline, leucine or threonine, or for co-factors like thiamine. According to the invention, the auxotrophy of host cells is corrected by integration of the missing/defective gene as a component of the expression cartridge into the genome along with integration of the gene of interest. The thus obtained prototrophic cells can be easily selected by growing them on a so-called "minimal medium" (prototrophic selection), which does not contain the compound for which the original host cell is auxotroph, thus allowing only positive clones to grow.

Prototrophic selection is independent of the integration locus. The integration locus for prototrophic selection may be any gene in the genome or at the locus carrying the auxotrophic marker. The particular advantage of prototrophic selection is that no antibiotic resistance marker nor any other marker that is foreign to the host remains in the genome after successful integration. Consequently, there is no need for removal of said marker genes, providing a fast and simple cloning and selection procedure. Another advantage is that restoring the gene function is beneficial to the cell and provides a higher stability of the system.

Alternatively, also shown schematically in FIG. 8, the marker gene that is inserted into the genome together with the expression cartridge, may be a metabolic gene that allows a particular selection mode. Such a metabolic gene may enable the cell to grow on particular (unusual) sugar or other carbon sources, and selection of positive clones can be achieved by growing cells on said sugar as the only carbon source.

As described above, during long term cultivation of bacteria, adaptive evolution (Herring et al, 2006) may cause an enhanced mutation frequency at the integration site during expression of the chromosomally encoded recombinant protein. The use of an auxotrophic knockout mutant strain in combination with an expression cartridge complementing the lacking function of the mutant strain (thereby generating a prototroph strain from an auxotroph mutant) has the additional advantage that the restored gene provides benefits to the cell by which the cell gains a competitive advantage such that cells in which adaptive evolution has occurred are repressed. Thereby, a means of negative selection for mutated clones is provided.

In some embodiments (in the case that the protein of interest allows for detection on a single-cell or single-colony basis, e.g. by FACS analysis or immunologically (ELISA)), no marker gene is required, since positive clones can be determined by direct detection of the protein of interest.

Other Features

The integration methods for obtaining the expression host cell are not limited to integration of one gene of interest at one site in the genome; they allow for variability with regard to both the integration site and the expression cassettes. By way of example, more than one genes of interest may be inserted, i.e. two or more identical or different sequences under the control of identical or different promoters can be integrated into one or more different loci on the genome. By way of example, it allows expression of two different proteins that form a heterodimeric complex. Heterodimeric proteins consist of two individually expressed protein subunits, e.g. the heavy and the light chain of a monoclonal antibody or an antibody fragment (Andersen and Reilly, 2004; Holliger and Hudson, 2005). Examples for other heterodimeric proteins are for instance CapZ (Remmert et al., 2000), Ras farnesyltransferase (Tsao and Waugh, 1997), platelet-activating factor acetylhydrolase Ib (Sheffield et al., 2001) or human DNA helicase II (Ochem et al., 1997). These two sequences encoding the monomers may be present on one expression cartridge which is inserted into one integration locus. Alternatively, these two sequences may be also present on two different expression cartridges, which are inserted independently from each other at two different integration loci. In any case, the promoters and the induction modes may be either the same or different.

Although the invention allows plasmid-free production of a protein of interest, it does not exclude that in the expression host cell a plasmid may be present that carries sequences to be expressed other than the gene of interest, e.g. the helper proteins and/or the recombination proteins described above. Naturally, care should be taken that in such embodiments the advantages of the invention should not be overruled by the presence of the plasmid, i.e. the plasmid should be present at a low copy number and should not exert a metabolic burden onto the cell.

Genome-based expression of recombinant proteins provides the following major advantages:

With respect to the construction procedure of the expression host, the advantages are (i) a simple method for synthesis and amplification of the linear insertion cartridge, (ii) a high degree of flexibility (i.e. no limitation) with respect to the integration locus, (iii) a high degree of flexibility with respect to selection marker and selection principle, (iv) the option of subsequent removal of the selection marker, (v) the discrete and defined number of inserted expression cartridges (usually one or two).

The expression system useful in the method of the invention may be designed such that it is essentially or completely free of phage functions.

Integration of one or more recombinant genes into the genome results in a discrete and pre-defined number of genes of interest per cell. In the embodiment of the invention that inserts one copy of the gene, this number is usually one (except in the case that a cell contains more than one genomes, as it occurs transiently during cell division), as compared to plasmid-based expression which is accompanied by copy numbers up to several hundred. In the expression system used in the method of the present invention, by relieving the host metabolism from plasmid replication, an increased fraction of the cell's synthesis capacity is utilized for recombinant protein production. Strong promoters, such as the T7 system, can be applied without adverse effects on host metabolism by reduction of the gene dosage.

A particular advantage is that the expression system has no limitations with regard to the level of induction. This means that the system cannot be "over-induced" as it often occurs in plasmid-based systems, where PCN may strongly increase upon induction (Teich et al., 1998; Wrobel and Wegrzyn, 1998). A strong expression system in combination with a high and/or increasing gene dosage triggers a metabolic overload and leads to a dramatic loss of cell viability (Bently et al., 1990; Glick, 1995; Cserjan-Puschmann et al., 1999) and causes a significantly shortened period of product formation and a loss of overall yield.

As mentioned above, plasmid-based expression systems have the drawback that, during cell division, cells may lose the plasmid and thus the gene of interest. Such loss of plasmid depends on several external factors and increases with the number of cell divisions (generations). This means that plasmid-based fermentations are limited with regard to the number of generations (in conventional fermentations, this number is approximately between 20 and 50). In contrast, the genome-based expression system used in the method of the invention ensures a stable, pre-defined gene dosage for a practically infinite number of generations and thus theoretically infinite cultivation time under controlled conditions (without the disadvantage of the occurrence of cells that do not produce the protein of interest and with the only limitation of potentially occurring natural mutations as they may occur in any gene).

In the case of chemically-inducible promoters, the invention provides the particular advantage that the amount of inducer molecule, when e.g. added in a continuous mode according to Striedner et al (2003), is directly proportional to the gene dosage per cell, either constant over the entire cultivation, or changing over cultivation time at pre-defined values.

Thereby control of the recombinant expression rate can be achieved, which is of major interest to adjust the gene expression rate.

Since the genome-based expression system allows exact control of protein expression, it is particularly advantageous in combination with expression targeting pathways that depend or rely on well-controlled expression. In a preferred embodiment, the method of the invention includes secretion (excretion) of the protein of interest from the bacterial cytoplasm into the culture medium. The advantage of this embodiment is an optimized and sustained protein secretion rate, resulting in a higher titer of secreted protein as compared to prior art secretion systems. Secretion may occur by passive diffusion through the bacterial cell wall, or by active secretion into the periplasmic space, followed by diffusion or physico-chemical release (e.g. by using the StII signal sequence as described in U.S. Pat. No. 4,680,262 and in U.S. Pat. No. 4,963,495), or by direct translocation of the protein of interest from the cytoplasm into the culture medium (e.g. by methods as described by Choi and Lee, 2004).

As described above, the invention allows to design simplified processes, improved process predictability and high reproducibility from fermentation to fermentation. The process of the invention, employing the expression system described above, is conducted in the fed-batch or in the semi-continuous or continuous mode (i.e. in a chemostat), whereby the advantages of the genome-encoded expression system are optimally exploited. There are no limitations with respect to process parameters such as growth rate, temperature and culture medium components, except as defined by the host cell's requirements and as pre-defined by the selected promoter.

Another advantage relates to the choice of the inducer molecule: Most of the available systems for high-level expression of recombinant genes in E. coli are lac-based promoter-operator systems (Makrides, 1996). Lactose, the precursor of the native inducer 1,6-allolactose, a natural and inexpensive carbohydrate that is readily available in large amounts, has been considered as an alternative to IPTG, however, in the past, lactose was regarded as unsuitable for induction due to the problem of inducer exclusion on glucose media and degradation in the cell. The expression system used in the invention allows a carbon-limited cultivation with continuous supply of lactose as inducer (Striedner et al., 2003) and thus prevents the lactose exclusion, eliminates the decreasing induction level observed during conventional pulse induction with lactose (Hoffman et al., 1995) and enables a tight expression rate control even with lactose as inducer.

Importantly, the expression system used in the invention has the advantage of providing a high yield of recombinant protein, both with regard to protein concentration per volume culture medium (i.e. the titer) and with regard to protein content in the obtained biomass. This feature makes the expression system used in the invention superior compared to prior art expression systems.

Furthermore, the invention offers the advantage that selection of the expression host cell and/or the optimal design of the expression cartridge, can be easily achieved in preliminary screening tests. By way of example, in such preliminary screens a series of linear expression cartridges that vary with respect to at least one element that has an impact on expression properties of the protein of interest (expression level or qualitative features like biological activity), i.e. control elements (e.g. promoter and/or polymerase binding site) and/or sequence of the gene of interest (i.e. different codon usage variants) and/or targeting sequences for recombination and/or any other elements on the cartridge, like secretion leaders, is constructed. The cartridge variants are integrated into the genome of a pre-selected host cell and the resulting expression host variants are cultivated, including induction of protein expression, under controlled conditions. By comparing protein expression, the host cell variant showing the most favourable results in view of an industrial manufacturing process is selected. In a variation of this pre-screening approach, instead of determining the optimal expression cartridge, the optimal bacterial strain may be identified by integrating identical cartridges into a panel of different host cells. Since the integration strategy has the advantage of allowing integration of a discrete number of gene copies (e.g. only one) into the genome, pre-screening of various parameters may be done without interference by plasmid replication or changes in plasmid copy number.

Manufacturing Scale Production

According to the invention, the term "cultivating" (or "cultivation", also termed "fermentation") relates to the propagation of bacterial expression cells in a controlled bioreactor according to methods known in the industry.

Manufacturing of recombinant proteins is typically accomplished by performing cultivation in larger volumes. The term "manufacturing" and "manufacturing scale" in the meaning of the invention defines a fermentation with a minimum volume of 5 L culture broth. Usually, a "manufacturing scale" process is defined by being capable of processing large volumes of a preparation containing the recombinant protein of interest, and yielding amounts of the protein of interest that meet, e.g. in the case of a therapeutic protein, the demands for clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring and control of process parameters (pH, temperature, dissolved oxygen tension, back pressure, etc.). The behaviour of an expression system in a lab scale method does not allow to predict the behaviour of that system in the complex environment of a bioreactor.

It was surprisingly found in the experiments of the invention that an expression system based on genome integration is particularly advantageous for methods on a manufacturing scale (with respect to both the volume and the technical system) in combination with a cultivation mode that is based on feeding of nutrients, in particular a fed-batch process or a continuous or semi-continuous process (e.g. chemostat).

Fed-Batch Cultivation

In certain embodiments, the method of the invention is a fed-batch process.

Whereas a batch process is a cultivation mode in which all the nutrients necessary for cultivation of the cells are contained in the initial culture medium, without additional supply of further nutrients during fermentation, in a fed-batch process, after a batch phase, a feeding phase takes place in which one or more nutrients are supplied to the culture by feeding. The purpose of nutrient feeding is to increase the amount of biomass (so-called "High-cell-density-cultivation process" or "HCDC") in order to increase the amount of recombinant protein as well. Although in most cultivation processes the mode of feeding is critical and important, the present invention is not restricted with regard to a certain mode of feeding.

Feeding of nutrients may be done in a continuous or discontinuous mode according to methods known in the art. The feeding mode may be pre-defined (i.e. the feed is added independently from actual process parameters), e.g. linear constant, linear increasing, step-wise increasing or following a mathematical function, e.g. exponential feeding.

In a preferred embodiment, the method of the invention is a fed-batch process, wherein the feeding mode is predefined according to an exponential function. By applying an exponential feeding mode, the specific growth rate μ of the cell population can be pre-defined at a constant level and optimized with respect to maximum recombinant protein expression. Control of the feeding rate is based on a desired specific growth rate μ. When a defined medium, as described below, is used, growth can be exactly predicted and pre-defined by the calculation of a biomass aliquot to be formed based on the substrate unit provided.

In another preferred embodiment, an exponential feeding mode may be followed, in the final stages of cultivation, by linear constant feeding.

In another embodiment of the fed-batch process, linear constant feeding is applied. Linear constant feeding is characterized by the feeding rate (volume of feed medium per time unit) that is constant (i.e. unchanged) throughout certain cultivation phases.

In another embodiment of the fed-batch process, linear increasing feeding is applied. Linear increasing feeding is characterized by a feeding rate of feed medium following a linear function. Feeding according to a linear increasing function is characterized by a defined increase of feeding rate per a defined time increment.

In another embodiment of the fed-batch process of the invention, a feedback control algorithm is applied for feeding (as opposed to a pre-defined feeding mode). In a feedback-controlled fed-batch process, the feeding rate depends on the actual level of a certain cultivation parameter. Cultivation parameters suitable for feedback-controlled feeding are for instance biomass (and chemical or physical parameters derived thereof), dissolved oxygen, respiratory coefficient, pH, or temperature (e.g. as described by Jahic et al., 2003). Another example for a feedback controlled feeding mode is based on the actual glucose concentration in the bioreactor (Kleman et al., 1991).

Continuous and Semi-Continuous Cultivation Mode

In another embodiment, bacterial cells carrying a genome-based expression cassette according to the present invention are cultivated in continuous mode (chemostat). A continuous fermentation process is characterized by a defined, constant and continuous rate of feeding of fresh culture medium into the bioreactor, whereby culture broth is at the same time removed from the bioreactor at the same defined, constant and continuous removal rate. By keeping culture medium, feeding rate and removal rate at the same constant level, the cultivation parameters and conditions in the bioreactor remain constant (so-called "steady state"). The specific growth rate μ can be pre-defined and is exclusively a result of the feeding rate and the culture medium volume in the bioreactor. Since cells having one or more genome-based expression cassettes are genetically very stable (as opposed to structurally and segregationally instable plasmid-based expression systems, or expression systems which genome-inserted cassette relies on genomic amplification), the number of generations (cell doublings) of cells according to the invention is theoretically unlimited, as well as, consequently, cultivation time. The advantage of cultivating a genetically stable genome-based expression system in a continuous mode is that a higher total amount of recombinant protein per time period can be obtained, as compared to genetically unstable prior art systems. In addition, due to the theoretically unlimited time of cultivation, continuous cultivation of cells according to the invention may lead to a higher total protein amount per time period even compared to fed-batch cultivation processes. In Example 7, the high stability and productivity of a genome-based expression construct is shown.

Another preferred embodiment refers to semi-continuous cultivation of cells. A semi-continuous cultivation process in the meaning of the invention is a process which is operated in its first phase as a fed-batch process (i. e. a batch phase followed by a feeding phase). After a certain volume or biomass has been obtained (i.e. usually when the upper limit of fermenter volume is obtained), a significant part of cell broth containing the recombinant protein of interest is removed from the bioreactor. Subsequently, feeding is initiated again until the biomass or volume of culture broth has again reached a certain value. This method (draining of culture broth and re-filling by feeding) can be proceeded at least once, and theoretically indefinite times.

Culture Medium

With regard to the type of the culture medium used in the fermentation process, there are no limitations. The culture medium may be semi-defined, i.e. containing complex media compounds (e.g. yeast extract, soy peptone, casamino acids), or it may be chemically defined, without any complex compounds.

Preferably, a "defined medium" is used. "Defined" media (also termed "minimal" or "synthetic" media) are exclusively composed of chemically defined substances, i.e. carbon sources such as glucose or glycerol, salts, vitamins, and, in view of a possible strain auxotrophy, specific amino acids or other substances such as thiamine. Most preferably, glucose is used as a carbon source. Usually, the carbon source of the feed medium serves as the growth-limiting component which controls the specific growth rate.

In the methods of the invention, significantly higher yields are obtained, because growth of bacteria and a high, but physiologically tolerable recombinant gene expression rate can be maintained during the whole production process.

Induction Mode

As described above, in a most preferred embodiment of the invention, the protein of interest is under control of an "inducible" or "controllable" promoter.

There is no limitation as regards the mode by which induction of protein expression is performed. By way of example, the inductor can be added as a singular or multiple bolus or by continuous feeding, the latter being also known as "inductor feed(ing)". There are no limitations as regards the time point at which the induction takes place. The inductor may be added at the beginning of the cultivation or at the point of starting continuous nutrient feeding or after (beyond) the start of feeding.

Inductor feeding may be accomplished by either having the inductor contained in the culture medium or by separately feeding it.

The advantage of inductor feeding is that it allows to control inductor dosage, i.e. it allows to maintain the dosage of a defined or constant amount of inductor per constant number of genes of interest in the production system. For instance, inductor feeding allows an inductor dosage which is proportional to the biomass, resulting in a constant ratio of inductor to biomass. Biomass units on which the inductor dosage can be based, may be for instance cell dry weight (CDW), wet cell weight (WCW), optical density, total cell number (TCN; cells per volume) or colony forming units (CFU per volume) or on-line monitored signals which are proportional to the biomass (e.g. fluorescence, turbidity, dielectric capacity, etc.). Essentially, the method of the invention allows the precise dosage of inductor per any parameter or signal which is proportional to biomass, irrespective of whether the signal is measured off-line or on-line. Since the number of genes of interest is defined and constant per biomass unit (one or more genes per cell), the consequence of this induction mode is a constant dosage of inductor per gene of interest. As a further advantage, the exact and optimum dosage of the amount of inductor relative to the amount of biomass can be experimentally determined and optimized, as demonstrated in Example 8 and FIG. 16 and FIG. 17.

It may not be necessary to determine the actual biomass level by analytical methods. For instance, it may be sufficient to add the inductor in an amount that is based on previous cultivations (historical biomass data). In another embodiment, it may be preferable to add the amount of inductor per one biomass unit as theoretically calculated or predicted. For instance, it is well known for feeding-based cultivations (like fed-batch or continuous) that one unit of the growth-limiting component in the feed medium, usually the carbon source, will result in a certain amount of biomass. As an example, 1 g glucose as growth-limiting substrate will result in approximately 0.33 g cell dry weight (also expressed by the substrate yield coefficient $Y_{X/S}$=0.33). Consequently, a defined dosage of inductor per gene of interest may also be achieved by the defined dosage of inductor per unit growth limiting-component, since a certain unit of growth limiting component results in a defined unit of biomass, and a defined unit of biomass contains a defined number of molecules of proteins of interest according to the method of the invention.

The concentration of IPTG may be in the range of 0.1-30 µg per g CDW, preferably, it is in the range of 0.5-20 µg per g CDW.

In Example 8, the maximum inductor dosage in the feed medium is 20 µmol IPTG per g CDW, which is equivalent to 6.6 µmol IPTG per g glucose, under the assumption of a substrate yield coefficient of $Y_{X/S}$=0.33. Consequently, since the glucose concentration in the feeding medium is 128 g/L, the IPTG concentration in the same medium was 844 µM.

As an essential advantage, feeding limiting amounts of inductor prevents metabolic load and reduces stress in favour of maximizing the capacity of protein synthesis.

The ratio of inductor per biomass (or per gene or per unit growth-limiting substrate) may not necessarily be constant. It may also be linear increasing, linear decreasing, increasing or decreasing according to exponential or other mathematical functions, etc. The essential feature according to the invention is that the value of inductor dosage per gene of interest is defined.

In certain embodiments, the method of the invention is a fed-batch process, wherein the inductor is present in the batch medium from start of cultivation.

The mode of induction of expression can also be constitutive, which means that induction is not triggered chemically or by other stimuli, but that it is permanent from start of cultivation. Constitutive induction is the preferred induction mode for continuous cultivation, but also useful for fed-batch cultivation.

EXAMPLES

Example 1

Figure 1:
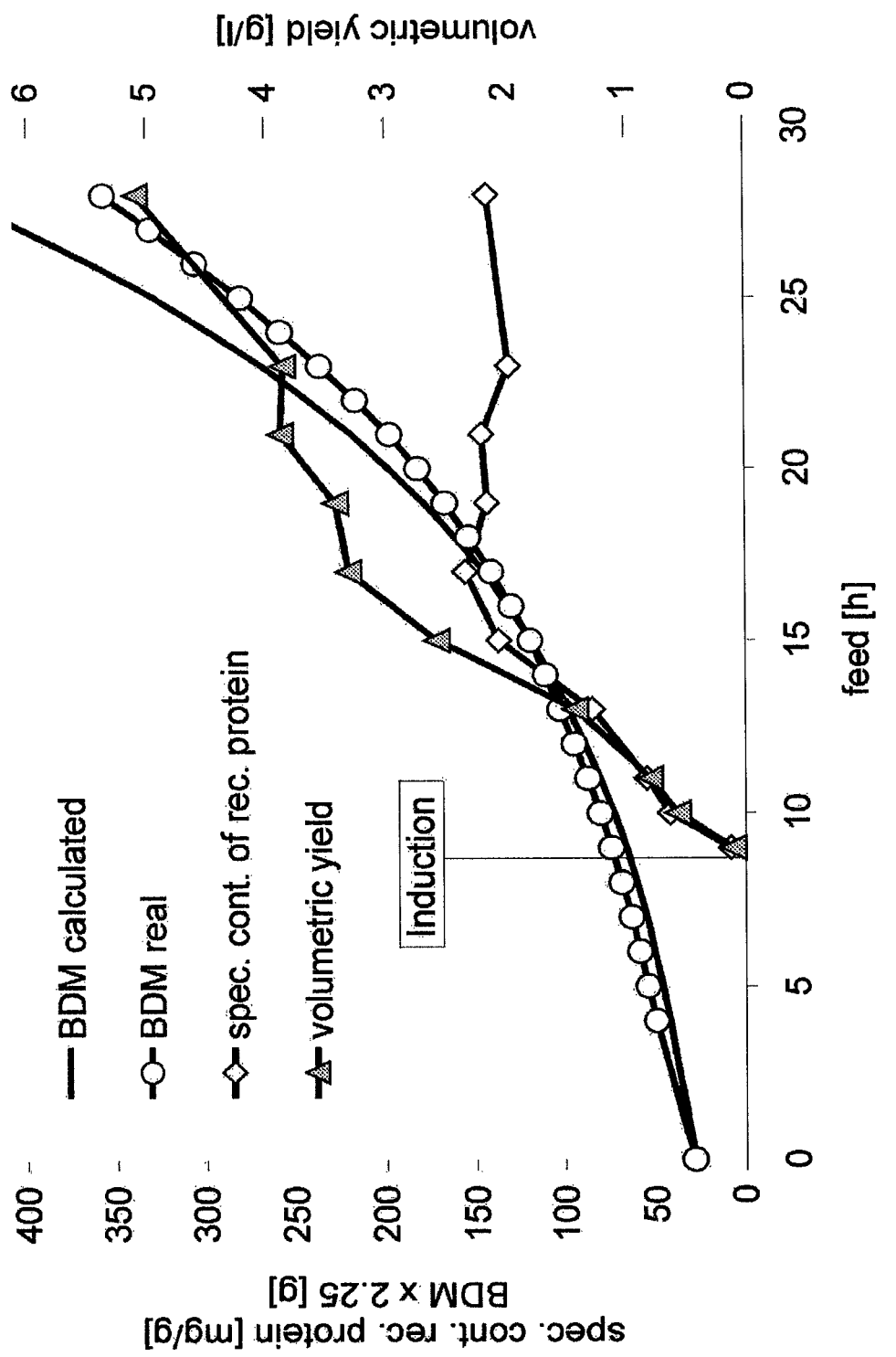
FIG. 1: Fed-batch cultivation employing genome-encoded expression system HMS174(DE3)<Cam:T7:6×His-NproEddieGFPmut3.1> for production of an insoluble autoprotease fusion protein (ES4).

Generation of Bacterial Strains and Description of Recombinant Proteins

Experiments are performed either with the recA⁻ K12 strain *E. coli* HMS174(DE3) or with the B-strain BL21 (DE3) provided by Novagen. The designation (DE3) indicates that the hosts are lysogens of λ DE3 prophage, carrying a chromosomal copy of the T7 RNA polymerase gene under control of the lacUV5 promoter, making these strains suitable for protein expression using T7 or T7 lac promoters (Studier and Moffat, 1986; Studier et al., 1990). Integration of linear DNA cartridges into the bacterial chromosome is done in *E. coli* MG1655 carrying the Red helper plasmid pKD46 as described by Datsenko and Wanner (2000). The linear expression cartridge is integrated into the attTn7 site, which is between the glmS gene and the pstS gene at the genome of *E. coli*. PCR verification of cassettes on the genome is done by combining external primers annealing to the genome and internal primers. By P1 transduction (Sternberg and Hoess, 1983; and Lennox, 1955), the recombinant chromosomal section is transferred into the expression hosts HMS174(DE3) and BL21(DE3). To act as a recipient, the recA deficient strain MS174(DE3) is used that contains the temperature-sensitive pTSA29-recA helper plasmid, providing the RecA protein (Phillips, 1998).

Reference experiments with prior art plasmid-based expression of target proteins are performed with pET30a and pET11a plasmids from Novagen (pET System manual, 11$^{th}$ edition).

To show the potential of the expression system of the invention, a soluble protein (Green Fluorescent Protein GFP; Shimomura et al., 1962)) and an inclusion body forming protein (Npro) are used in the experiments. GFPmut3.1 is a FACS-optimised variant (Cormack et al., 1996) with substitutions S65G and S72A for improved folding and excitation at 488 nm. The inclusion body forming protein 6xHis-N$^{pro}$Eddie-GFPmut3.1 is a fusion of the above-described GFPmut3.1 and N$^{pro}$Eddie, a modified variant (described in WO 2006/113959) of the native N$^{pro}$ autoprotease from classical swine fever virus (Thiel et al., 1991). N$^{pro}$ is a non-structural protein consisting of 168 amino acids (apparent Mr of 23000), which cleaves itself co-translationally from the nascent polyprotein, thereby generating the correct N-terminus of the capsid protein C (Wiskerchen et al., 1991; Stark et al., 1993).

TABLE 1

List of generated expression systems.

| Abbreviation of expression system | Strain | Location of gene of interest | Designation of plasmid or integration cartridge/ target protein (underlined: protein the respective system is encoding) | Described in Example |
|---|---|---|---|---|
| ES1 | HMS174(DE3) | Plasmid | (pET30a 6xHis-N$^{pro}$Eddie-GFPmut3.1) | Example 3 |
| ES2 | BL21(DE3) | Plasmid | (pET30a 6xHis-N$^{pro}$Eddie-GFPmut3.1) | Example 4 |
| ES3 | HMS174(DE3) | Plasmid | (pET11a GFPmut3.1) | Example 5 |
| ES4 | HMS174(DE3) | Genome | <Cam:T7:6xHis-N$^{pro}$Eddie-GFPmut3.1> | Example 3 |
| ES5 | BL21(DE3) | Genome | <Cam:T7: 6xHis-N$^{pro}$Eddie-GFPmut3.1> | Example 4 |
| ES6 | HMS174(DE3) | Genome | <Kan:T7 GFPmut3.1> | Example 5 and Example 7 |
| ES7 | HMS174(DE3) | Plasmid | (pET11ahSOD) | Example 6 |
| ES8 | HMS174(DE3) | Genome | <Cam:T7: hSOD> | Example 6 |
| ES9 | BL21(DE3) | Genome | <Cam:T7: hSOD> | Example 6 |
| ES10 | BL21(DE3) | Genome | <Cam:T7: GFPmut3.1> | Example 8 |

Example 2

Cultivation Mode and Process Analysis

The cells are grown either in a 7 L (5 L net volume, 2.5 L batch volume) or in a 20 L (12 L net volume, 8 L batch volume) computer-controlled bioreactor (MBR; Wetzikon, CH) equipped with standard control units. The pH is maintained at a set-point of 7.0±0.05 by addition of 25% ammonia solution (ACROS Organics), the temperature is set to 37° C.±0.5° C. In order to avoid oxygen limitation, the dissolved oxygen level is stabilized above 30% saturation by stirrer speed and aeration rate control. The content of $O_2$ and $CO_2$ in the outlet air is determined by a Hartmann and Braun Advanced Optima gas analyzer. Dielectric capacity and conductivity are measured with the Biomass monitor, model 214M (Aber Instruments, Aberystwyth, UK) set. Fluorescence measurements are performed using a multi-wavelength spectrofluorometer specially designed for online measurements in an industrial environment, the BioView® (DELTA Light & Optics, Lyngby, Denmark). Foaming is suppressed by addition of antifoam suspension (Glanapon 2000, Bussetti, Vienna) with a concentration of 1 ml/1 feed medium. For inoculation, a deep frozen (−80° C.) working cell bank vial, is thawed and 1 ml (optical density $OD_{600}$=1) is transferred aseptically to the bioreactor. Feeding is started when the culture, grown to a bacterial dry matter of 12.5 g in 2.5 L batch medium (or 30 g in 4 L batch medium), entered stationary phase. Fed-Batch regime with an exponential substrate feed is used to provide a constant growth rate of 0.1 h$^{−1}$ during 4 doubling times. The substrate feed is controlled by increasing the pump speed according to the exponential growth algorithm, $x=x_o \cdot e^{\mu t}$, with superimposed feedback control of weight loss in the substrate tank (Cserjan-Puschmann et al., 1999). The feed medium provided sufficient components to yield another 202 g (or 450 g) of bacterial dry matter.

Induction

Induction is performed in a conventional mode by a single pulse directly into the bioreactor. The supplied amount of IPTG is calculated to set a concentration of 1 μmol IPTG at the end of the process in order to gain a fully induced system.

Media Composition

The minimal medium used in this study contains 3 g $KH_2PO_4$ and 6 g $K_2HPO_4*3H_2O$ per litre. These concentrations provide the required buffer capacity and serve as P and K source as well. The other components are added in relation of gram bacterial dry matter to be produced: sodium citrate (trisodium salt*$2H_2O$; ACROS organics) 0.25 g, $MgSO_4*7H_2O$ 0.10 g, $CaCl_2*2H_2O$ 0.02 g, trace element solution 50 μl and glucose*$H_2O$ 3 g. In all experiments with expression systems ES6, ES7 and ESB, medium is supplemented with $CuCl_2*2H_2O$ 4 mg and $ZnSO_4*7H_2O$ 3.2 mg per gram bacterial dry matter. To accelerate initial growth of the population, the complex component yeast extract 0.15 g is added to the minimal medium to obtain the batch medium. For the feeding phase 2.5 L of minimal medium are prepared according to the amount of biological dry matter 202 g (or 450 g) to be produced in the feeding phase, whereby P-salts are again added per litre. Trace element solution: prepared in 5 N HCl (g/L): $FeSO_4*7H_2O$ 40.0, $MnSO_4*H_2O$ 10.0, $AlCl_3*6H_2O$ 10.0, $CoCl_2$ (Fluka) 4.0, $ZnSO_4*7H_2O$ 2.0, $Na_2MoO_2*2H_2O$ 2.0, $CuCl_2*2H_2O$ 1.0, $H_3BO_3$ 0.50.

Offline Analysis

Optical density (OD) is measured at 600 nm. Bacterial dry matter is determined by centrifugation of 10 ml of the cell suspension, re-suspension in distilled water followed by centrifugation, and re-suspension for transfer to a pre-weighed beaker, which is then dried at 105° C. for 24 h and re-weighed.

The progress of bacterial growth is determined by calculating the total amount of biomass (total bacterial dry matter BDM; also termed cell dry weight CDW).

Total Cell Number (TCN) and percentage of dead cells (DC) are determined using flow cytometric methods. All measurements are performed with a FACSCalibur flow cytometer (four-color system; Becton Dickinson), equipped with an air-cooled laser providing 15 mW at 488 nm and the standard filter setup. Samples are spiked with a known amount of fluorescent counting beads (Becton Dickinson, USA) so that the absolute cell number could be back-calculated.

The content of recombinant protein Npro-Eddie-GFPmut3.1 is determined by a combination of ELISA and electrophoretic protein quantification using the Agilent Bioanalyser. Soluble recombinant product is quantified via GFP-ELISA according to Reischer et al. (2004), while the recombinant product in the inclusion bodies is determined with the Agilent Bioanalyser 2100, using the Protein 200 LabChip® Kit.

The content of recombinant GFP is quantified via GFP-ELISA according to Reischer et al. (2004). The content of hSOD is quantified via SOD ELISA according to Bayer et. al (1990).

Plasmid-containing cells but also cells carrying the integration cassette are determined by cultivation on LB-agar plates and on plates containing 100 mg/ml Kanamycin respectively 100 mg/ml Ampicillin and by counting colony forming units (CFU) after 24 h.

Example 3

Expression of 6xHis-NproEddie-GFPmut3.1 as Insoluble Inclusion Body with E. coli HMS174(DE3) in the Fed-Batch Mode Expression systems ES1 and ES4 listed in Table 1 are used in order to characterize the behaviour of the expression system of the invention (ES4) for production of insoluble target proteins (i.e. as inclusion bodies), and to evaluate the economic potential compared to plasmid based expression systems (ES1). The experiment with the expression system of the invention shows high but physiologically tolerable gene expression rates. The product formation can be maintained for more than 20 hours. Induction is performed as single pulse one doubling past feed start in order to gain a fully induced system (FIG. 1).

Figure 2:
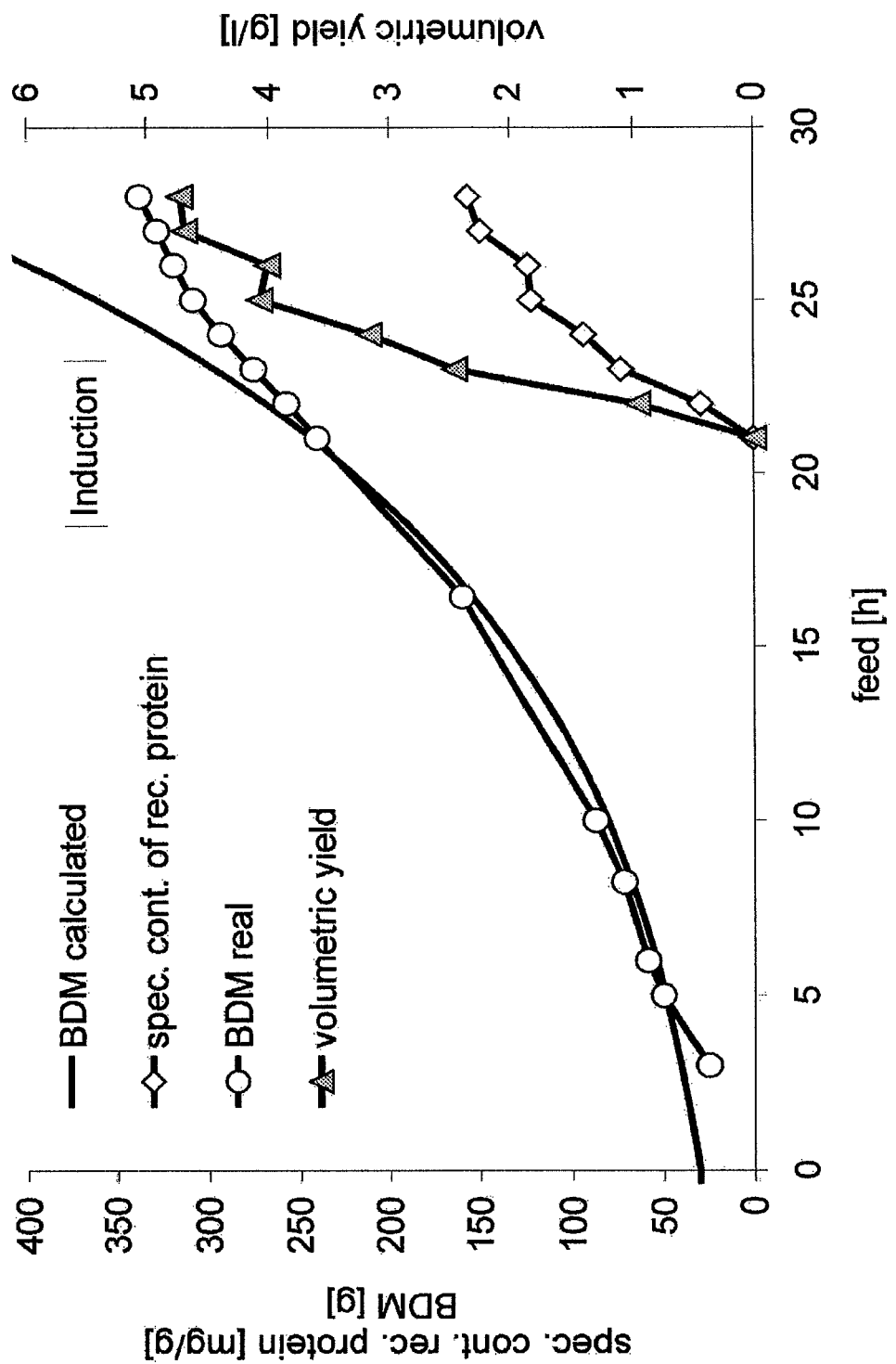
FIG. 2: Fed-batch cultivation employing plasmid-encoded expression system HMS174(DE3)(pET30a6×His-NproEddie-GFPmut3.1) for production of an insoluble autoprotease fusion protein (ES1).

In contrast to these results, the gene expression rate triggered by the plasmid based expression system over-strains the metabolic capacities of the cells and lead to the breakdown of the cellular system four hours past induction, performed as single IPTG pulse tree doublings past feed start (FIG. 2). Expression system ES4 according to the invention showed a slightly higher volumetric product yield (Table 2). As can be seen from these experiments, the expression system of the invention offers the advantage that process control and defined conditions can be maintained during the whole period of product formation.

TABLE 2

Summary of results from Example 3
(Comparison of genome-encoded and plasmid-encoded production of the protein 6xHis-NproEddie-GFPmut3.1 with the host strain HMS174(DE3).

|  | Genome encoded (ES1) | Plasmid-encoded (ES4) |
|---|---|---|
| Total yield of bacterial dry matter (BDM) [g] | 158 | 486 |
| Deviation of BDM yield in % from theoretically calculated BDM yield | 20 | 30 |
| Specific content of recombinant protein [mg/gBDM] | 144 | 156 |
| Volumetric yield (titer) of recombinant protein [g/L] | 5.0 | 4.7 |

Example 4

Figure 3:
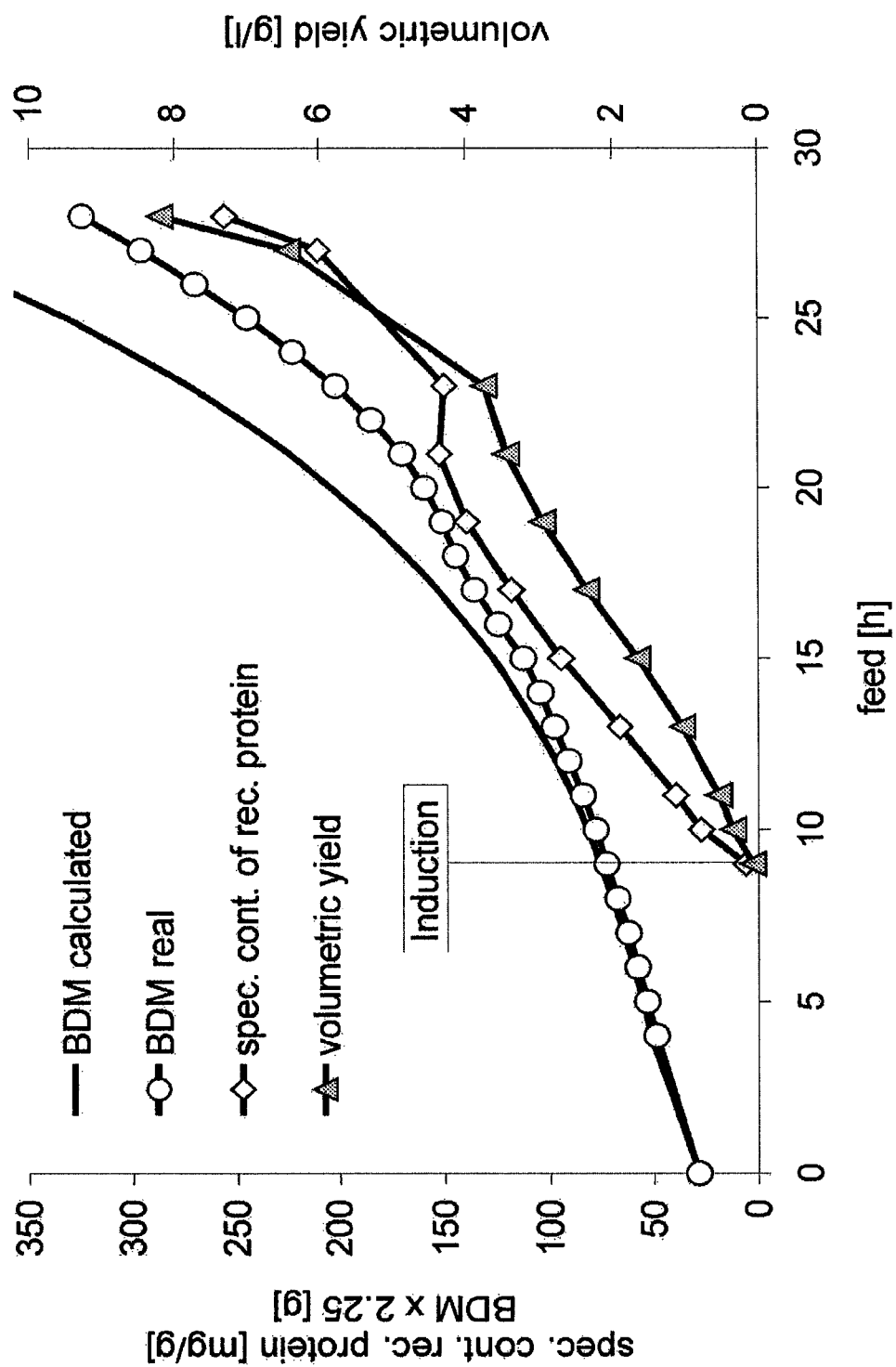
FIG. 3: Fed-batch cultivation employing genome-encoded expression system BL21(DE3)<Cam:T7:6×His-NproEddieGFPmut3.1> (ES5).
Figure 4:
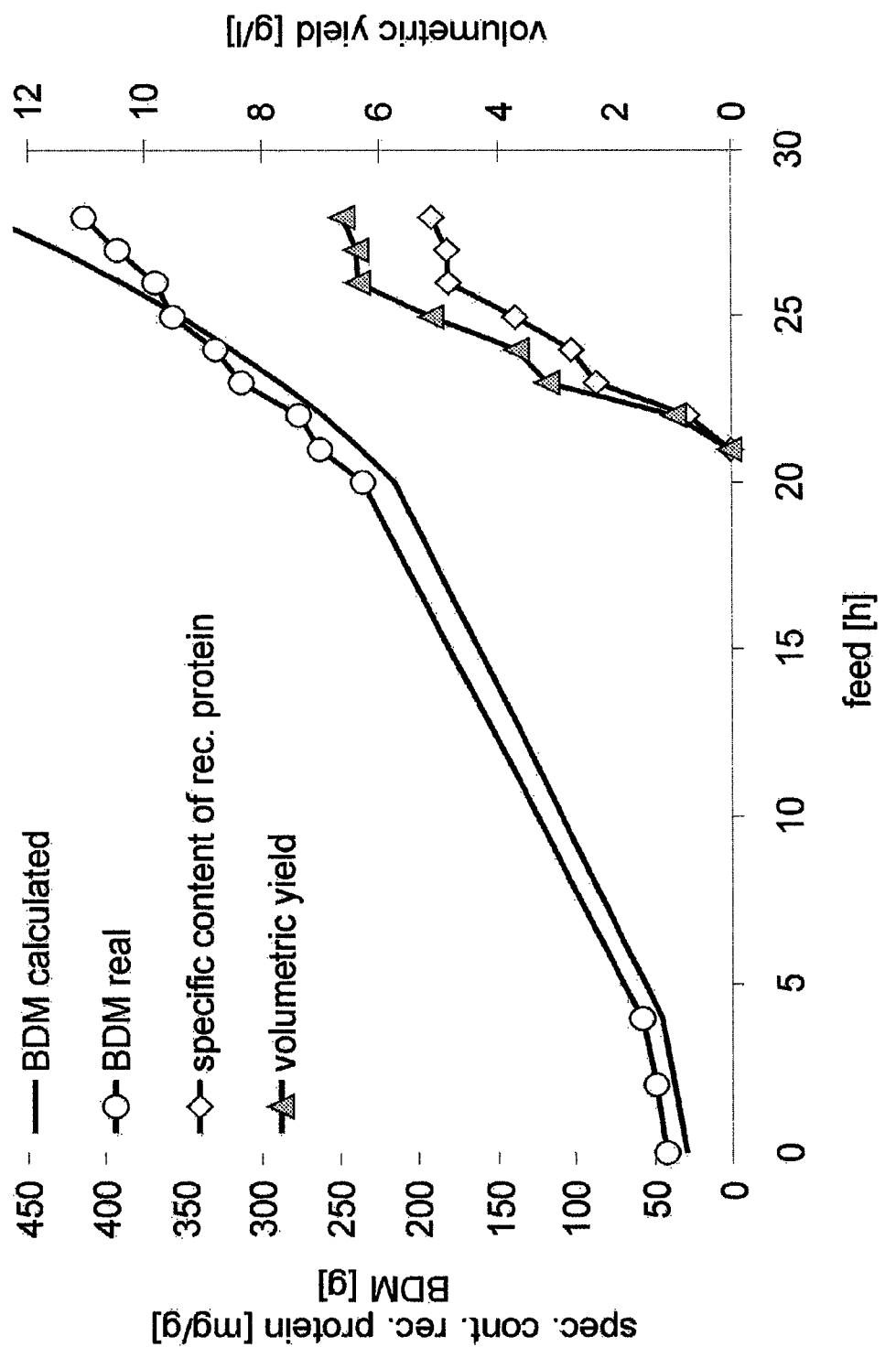
FIG. 4: Fed-batch cultivation employing plasmid-encoded expression system BL21(DE3)(pET30a6×His-Npro-GFPmut3.1) for production of an insoluble autoprotease fusion protein (ES2).

Expression of 6xHis-NproEddie-GFPmut3.1 as Insoluble Inclusion Body with E. coli BL21(DE3) in the Fed-batch Mode In order to prove the general applicability of the expression system of the invention, strain E. coli BL21(DE3) is used as expression host. ES5 of Table 1 is cultivated in the 5 L scale according to the procedure described above. The results of this system (FIG. 3; induction is performed as single pulse one doubling past feed) are better than the results with the K12 strain HMS174 and, compared to the results obtained with the plasmid-based ES2 (FIG. 4); induction is performed as single pulse tree doublings past feed start.), the system of the invention shows significantly higher product yields and higher process stability than the plasmid-based system (Table 3). The plasmid-based system of strain BL21 shows the same characteristics as described with strain HMS174, and too high product formation rates lead to the breakdown of the system and loss of process control.

TABLE 3

Summary of results from Example 4
(Comparison of genome-encoded and plasmid-encoded production of
the protein 6xHis-NproEddie-GFPmut3.1 with the host strain BL21(DE3).

|  | Genome encoded (ES5) | Plasmid-encoded (ES2) |
|---|---|---|
| Total yield of bacterial dry matter (BDM) [g] | 144 | 486 |
| Deviation of BDM yield in % from theoretically calculated BDM yield | 25 | 15 |
| Specific content of recombinant protein [mg/gBDM] | 256 | 192 |
| Volumetric yield (titer) of recombinant protein [g/L] | 8.2 | 6.6 |

Example 5

Figure 5:
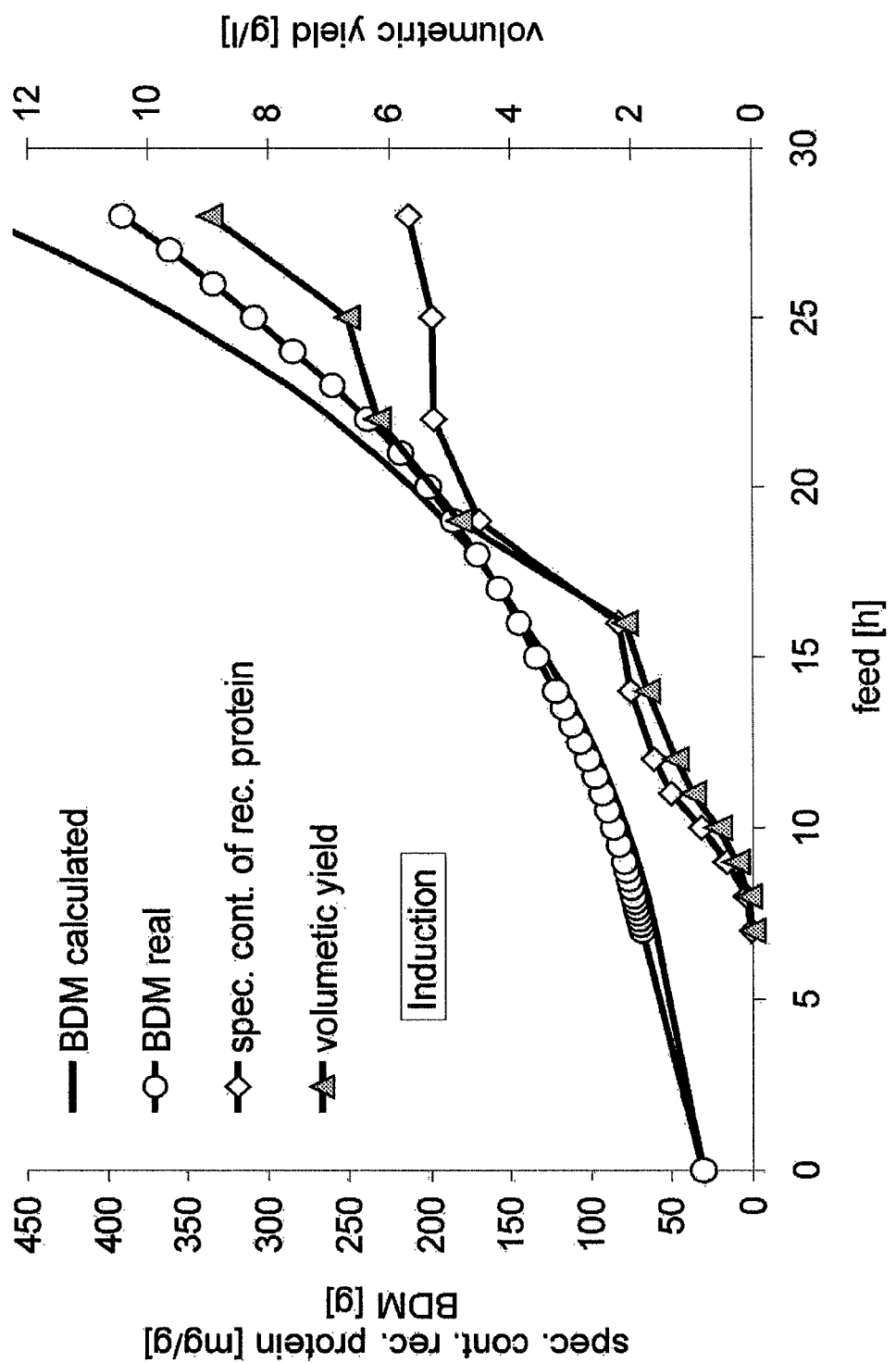
FIG. 5: Fed-batch cultivation employing genome-encoded expression system HMS174(DE3TN7::<Kan:T7GFPmut3.1> for production of the soluble green fluorescent protein (ES6).
Figure 6:
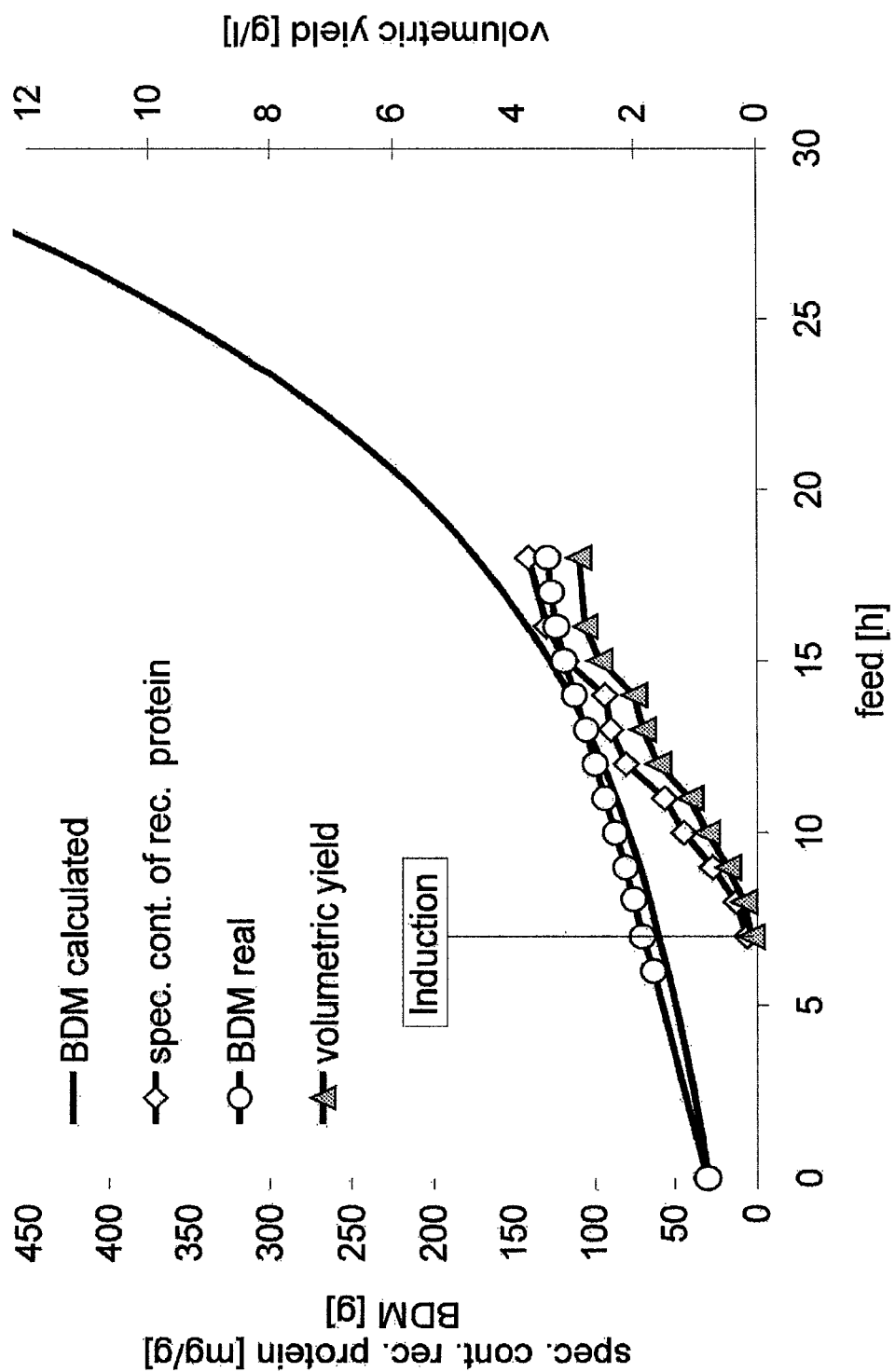
FIG. 6: Fed-batch cultivation employing plasmid-encoded expression system HMS174(DE3)(pET30a GFPmut3.1) for production of the soluble green fluorescent protein (ES3).
Figure 7:
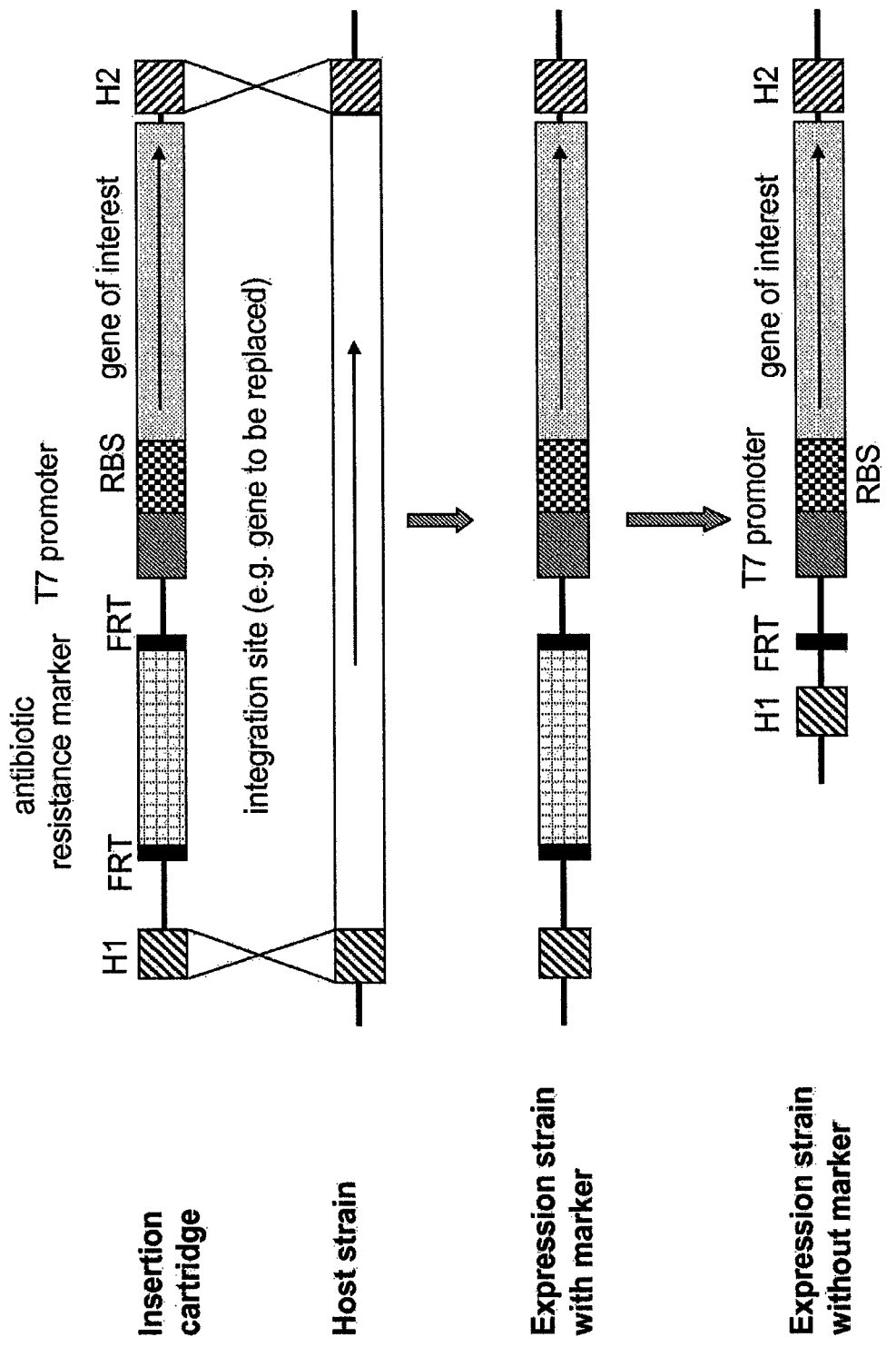
FIG. 7: Selection by insertion of an antibiotic resistance marker, optionally followed by removal (excision) of marker.
Figure 8:
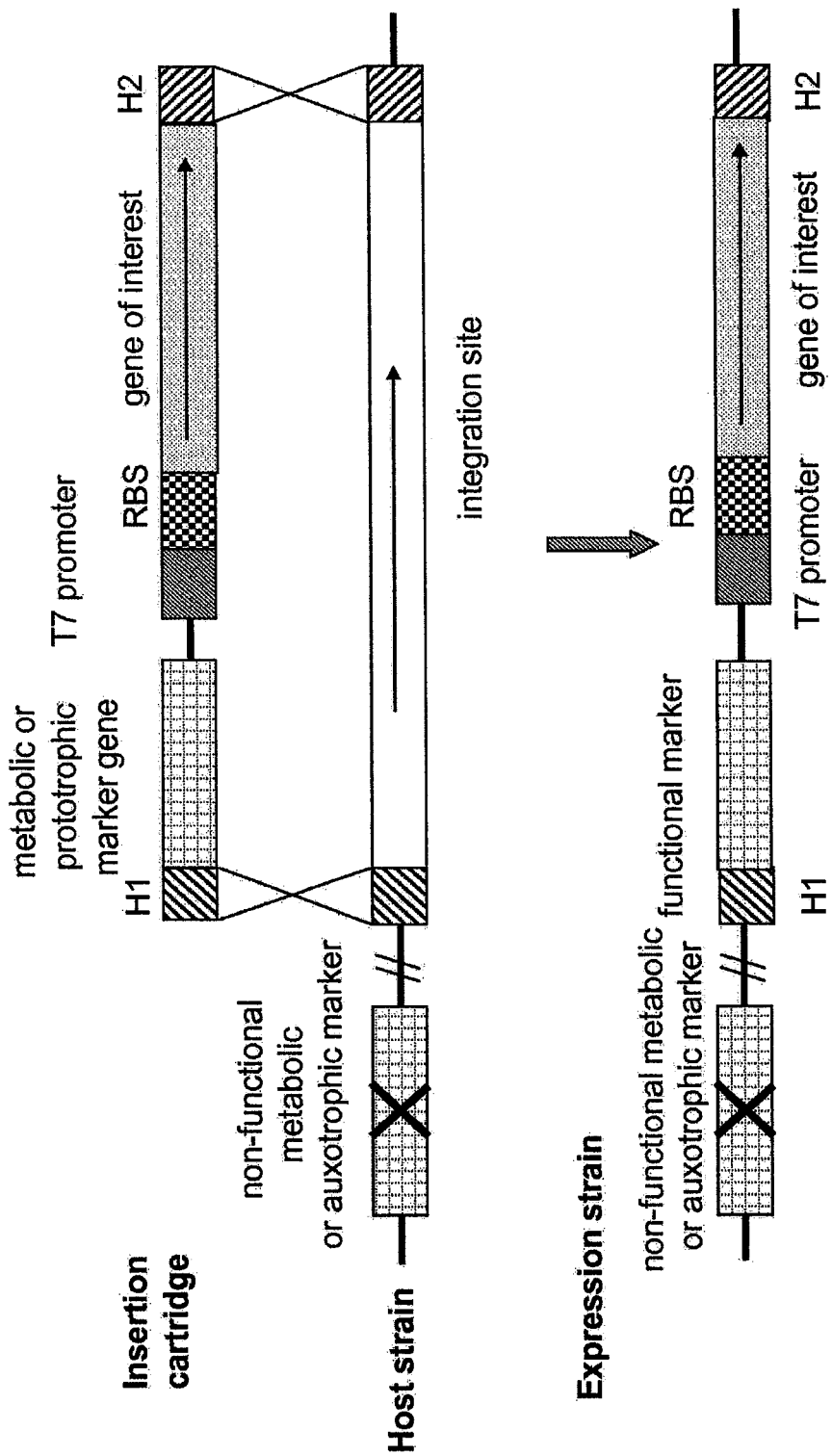
FIG. 8: Selection by providing a non-essential metabolic gene or a prototrophic complementation gene as marker.
Figure 9:
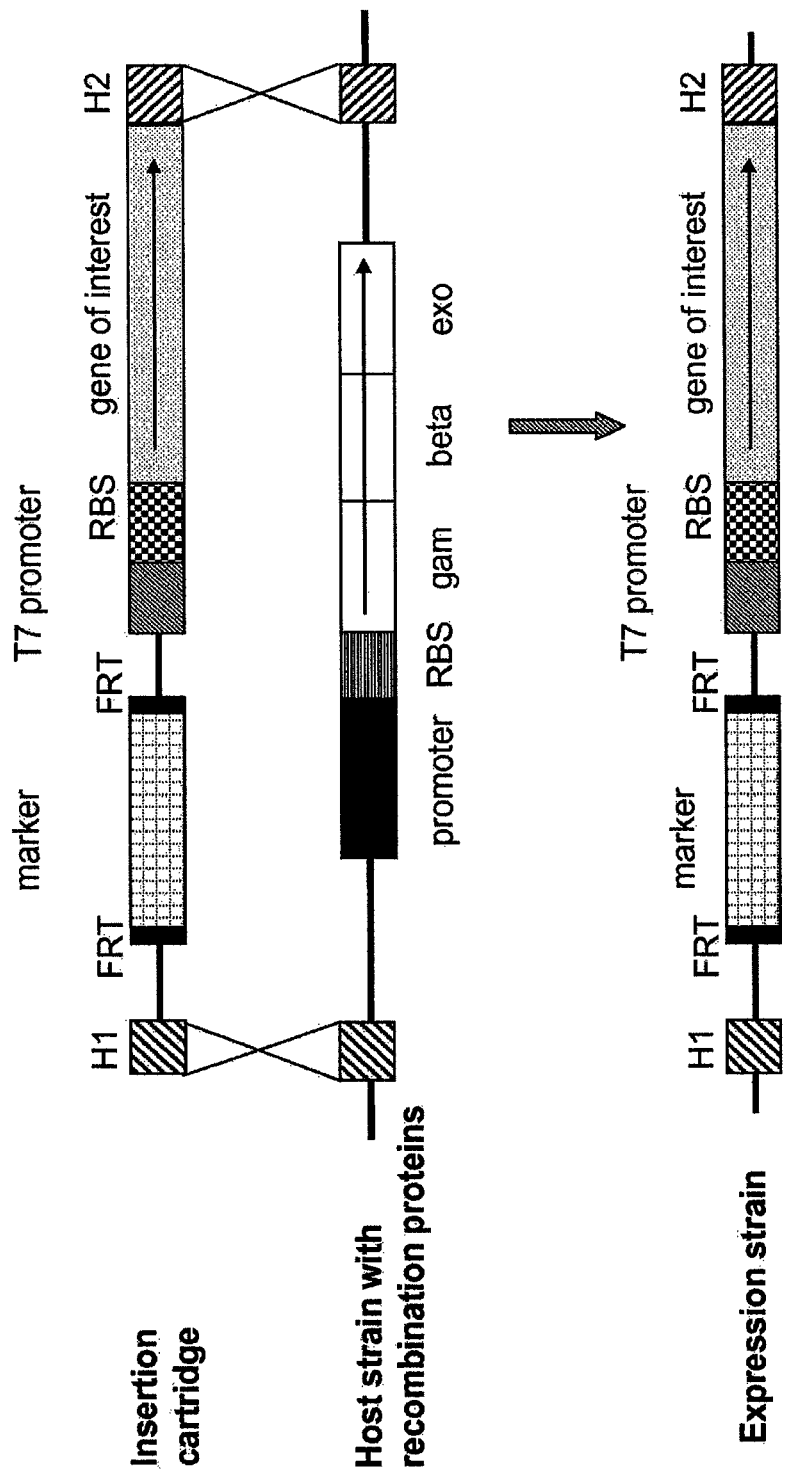
FIG. 9: Insertion of expression cartridge at the genomic site of recombination proteins, thereby removing them.
Figure 10:
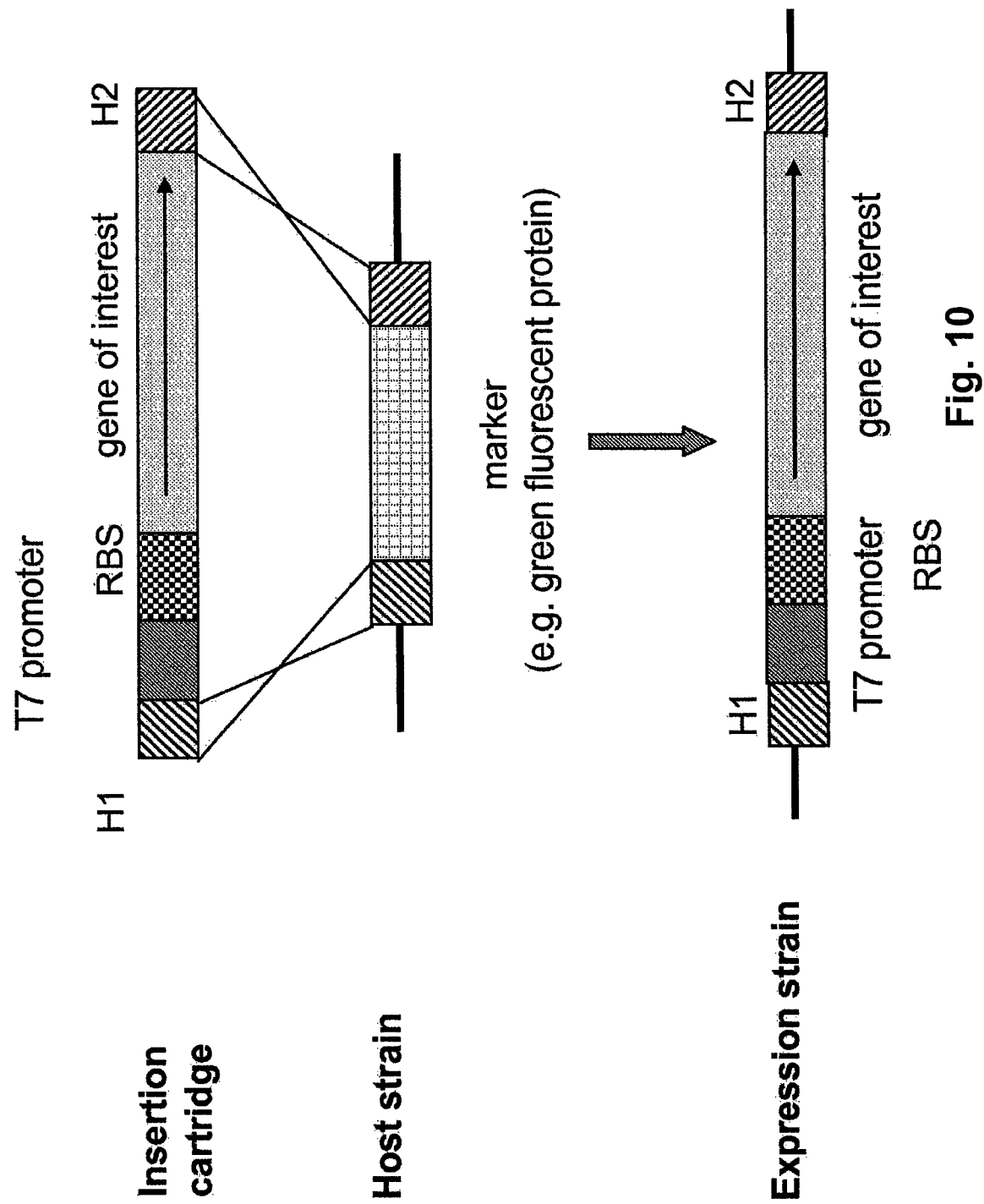
FIG. 10: Insertion of expression cartridge at the site of a marker gene, and selection for disappearance of marker phenotype.
Figure 11:
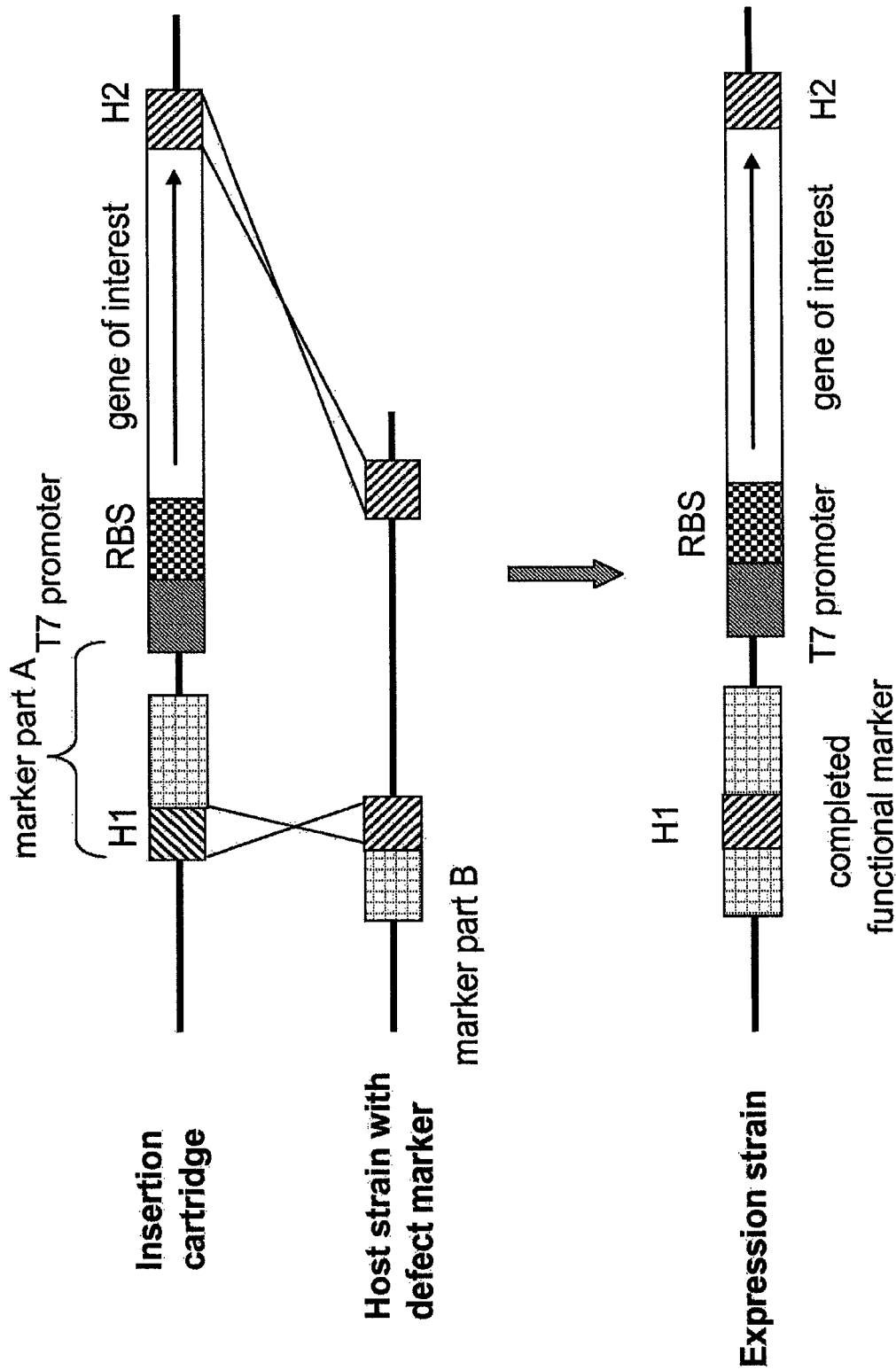
FIG. 11: Selection by completion of the missing part of a non-functional marker to generate a functional, selectable marker.

Expression of GFPmut3.1 as Soluble Protein with *E. coli* HMS174(DE3) in the Fed-Batch Mode Expression system ES3 and ES6 listed in Table 1 are used in order to characterise the behaviour of the expression system of the invention for production of soluble target proteins (the other expression systems of Table 1 form insoluble protein aggregates, i.e. inclusion bodies). In order to exclude effects triggered by different cell densities, identical cultivations with induction one doubling past feed start are performed, although the results of the other experiments demonstrated that the plasmid based systems triggers too high expression rates and cell activity cannot be maintained with this system. To cope with required comparability there is a third column in Table 4 called "plasmid-encoded optimized" which means that the results of ES2 "plasmid-encoded" are extrapolated to an experimental setup simulating induction at one doubling past start of feed. As can be derived from FIG. 5 and FIG. 6 (induction is performed as single pulse tree doublings past feed start) as well as from Table 4, the expression system of the invention proved to be more efficient. This is especially demonstrated by a higher specific and volumetric yield of recombinant protein and a better conversion rate of nutrients into biomass (i.e. a higher BDM yield or a lover deviation rate from the theoretical value).

TABLE 4

Summary of results from Example 5
(Comparison of genome-encoded and plasmid-encoded production
of the protein GFPmut3.1 with the host strain HMS174(DE3).

|  | Genome-encoded (ES6) | Plasmid-encoded (ES3) | Plasmid-encoded, optimized (ES3) |
|---|---|---|---|
| Total yield of bacterial dry matter (BDM) [g] | 391 | 129 | 356 |
| Deviation of BDM yield in % from theoretically calculated BDM yield | 19 | 26 | 26 |
| Specific content of recombinant protein [mg/gBDM] | 213 | 141 | 141 |
| Total rec. protein yield [g] | 101 | 18 | 50 |
| Volumetric protein yield (titer) [g/L] | 8.95 | 2.93 | 4.43 |

Example 6

Figure 12:
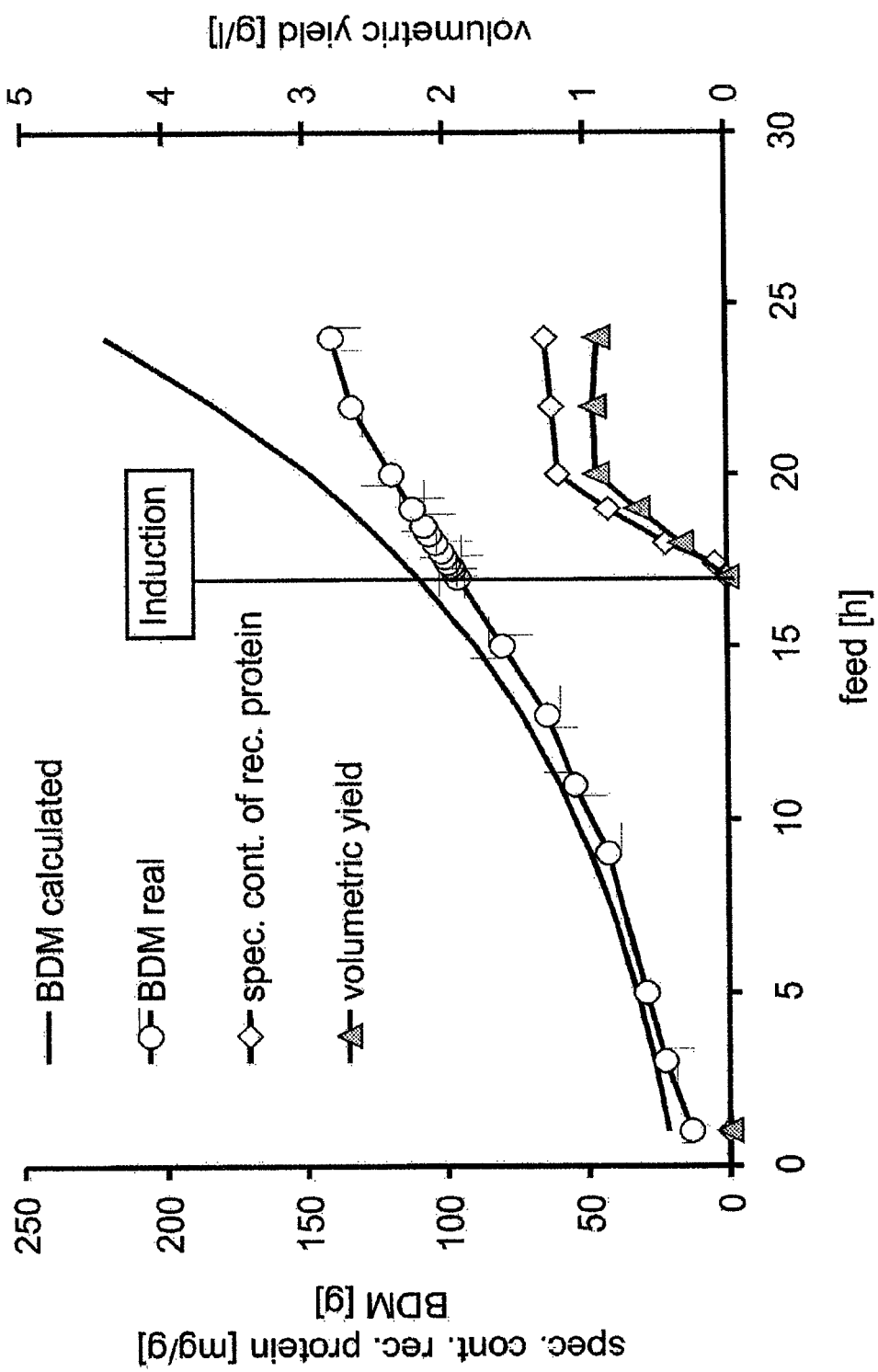
FIG. 12: Fed-batch cultivation employing plasmid-encoded expression system HMS174(DE3) for production of the soluble hSOD (ES7).
Figure 13:
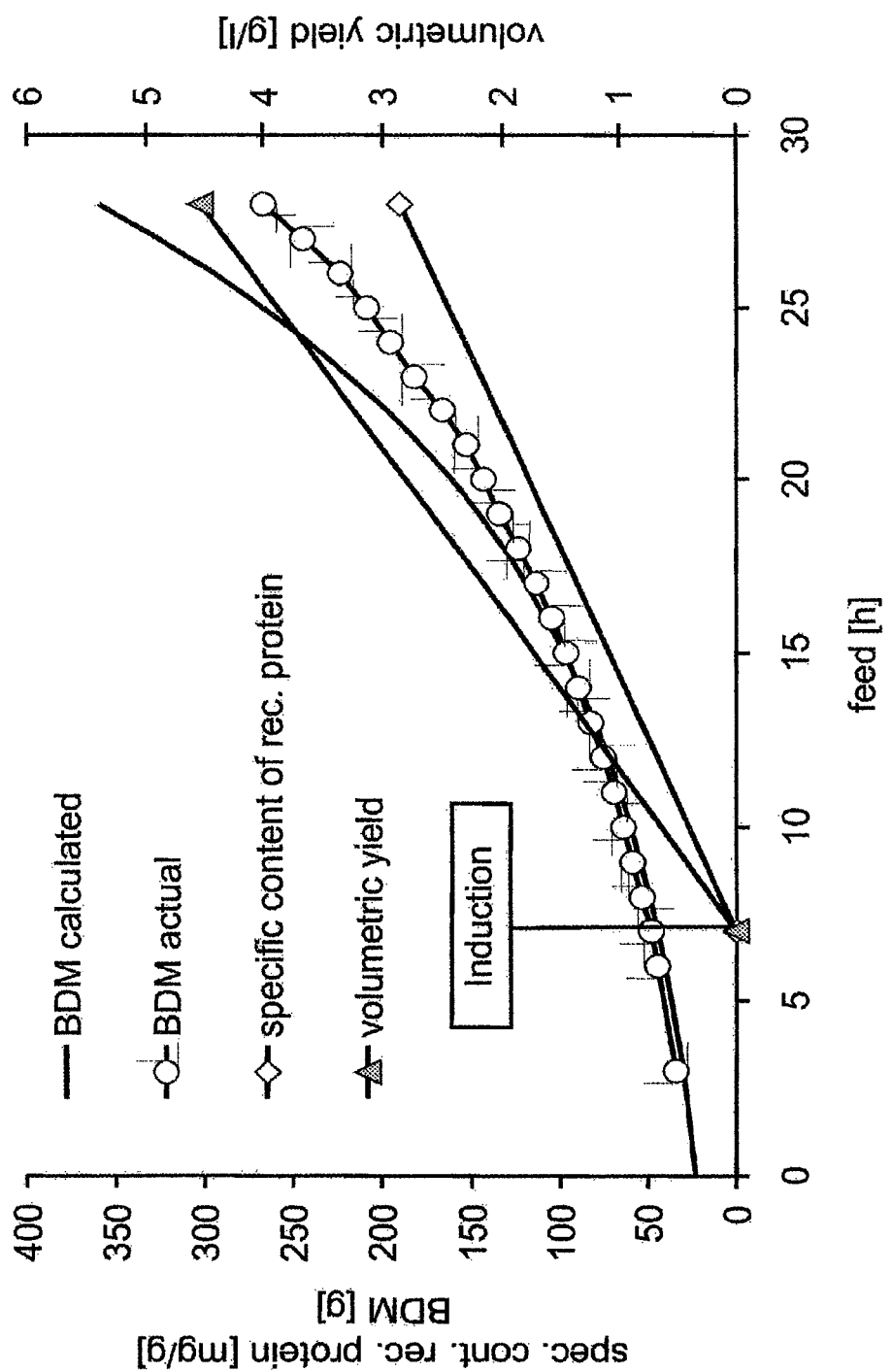
FIG. 13: Fed-batch cultivation employing genome-encoded expression system HMS174(DE3) for production of the soluble hSOD (ES8).
Figure 14:
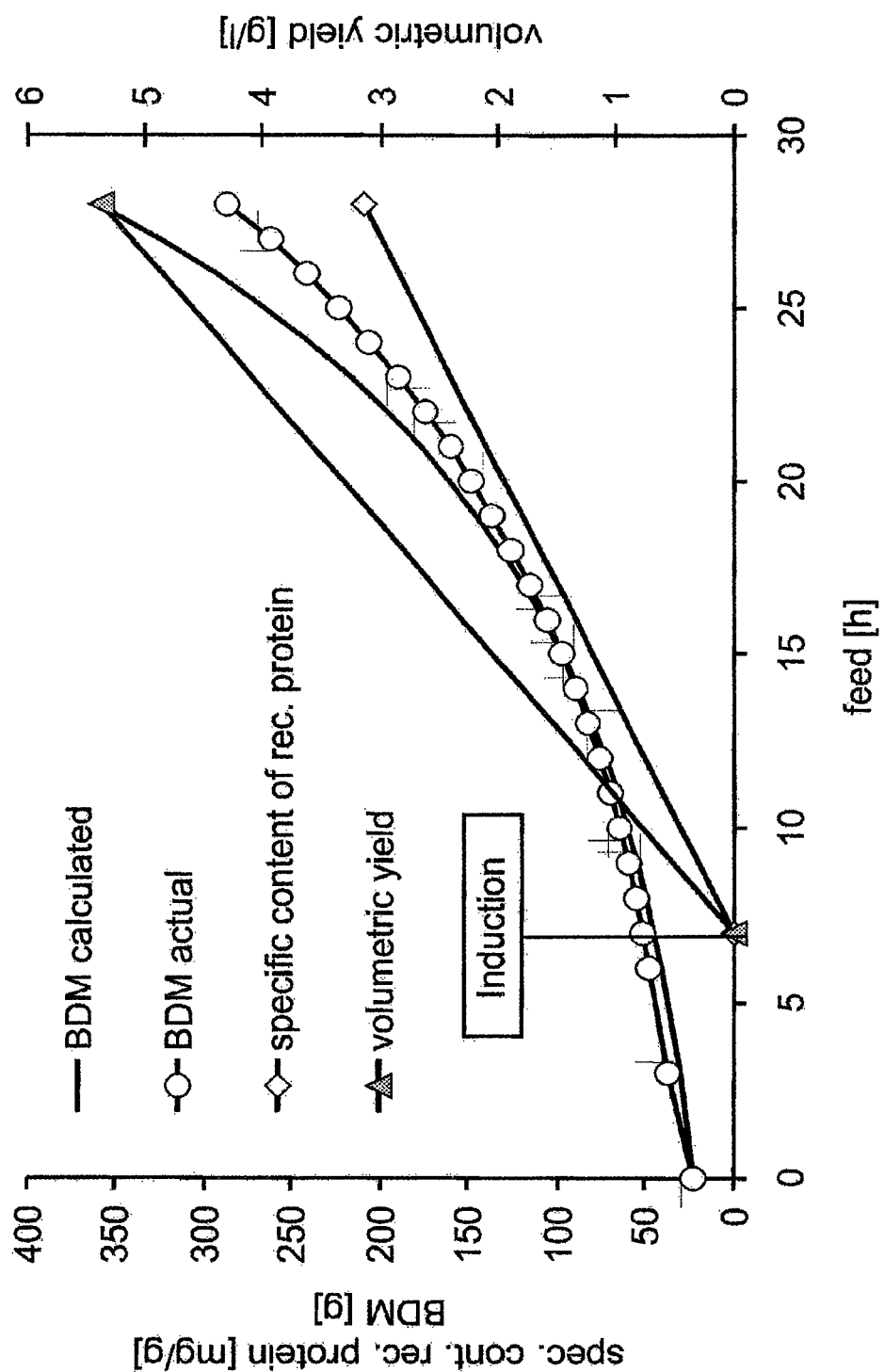
FIG. 14: Fed-batch cultivation employing genome-encoded expression system BL21 (DE3) for production of the soluble hSOD (ES9).

Expression of Soluble hSOD *E. coli* HMS174(DE3) and BL21(DE3) in Fed-batch Mode Recombinant human superoxide dismutase (hSOD) is produced by plasmid-based and by genome-based expression with *E. coli* HMS174(DE3) (ES7, ES8) and additionally by genome-based expression using *E. coli* BL21(DE3) (ES9). Human SOD is selected as third model protein because this enzyme is described as highly interactive in the bacterial cytosol, thereby representing a well suited protein candidate to investigate robustness and performance of the production method using genome-based expression. In the experiment with ES7 (FIG. 12) the amount of biological dry matter to be produced is pre-defined to 225 g BDM and induction is performed 2.5 doublings past feed start. In the cultivations with expression system ES8 (FIG. 13) and ES9 (FIG. 14) the calculated BDM is pre-defined to 360 g BDM and induction is performed at one doubling past start of feed. In order to allow proper comparison of ES7 and ES8, calculated values for total yield and the volumetric yield obtained in the experiment with ES7 are used as this experiment is run at a lower cell density and a smaller volume. The results in Table 5 show that the yields obtained with genome based ES8 are about 3-fold higher and the behavior during production is more robust and stable (indicated by a smaller difference between BDM calculated and BDM real). Even though there is a slight BDM deviation from the calculated course, growth can be maintained during the whole process indicating that genome encoded hSOD expression does not exceed the metabolic capacity of the cell which is in contrast to plasmid-encoded SOD expression. The results delivered by the experiment with genome-based ES9 (Table 5 column 4) show a further increase in yield of approximately 20% which means that the BL21(DE3) strain is even better suited for production of hSOD than the K12 strain.

TABLE 5

Summary of results from Example 5
(Comparison of genome-encoded and plasmid-encoded production of
the protein hSOD with the host strain HMS174(DE3), and production
of genome-encoded hSOD with strain BL21(DE3). Values marked
with * are calculated values to ensure comparability (due to the
fact that the plasmid encoded system is run at a lower cell density).

|  | HMS174(DE3) Plasmid-encoded ES7 | HMS174(DE3) Genome-encoded ES8 | BL21(DE3) Genome-encoded ES9 |
|---|---|---|---|
| Total yield of biomass dry matter (BDM) [g] | 140 | 360 | 391 |
| Deviation of BDM yield in % from theoretically calculated (pre-defined) BDM yield | 36 | 26 | 20 |
| Specific content of recombinant protein [mg/gBDM] | 64 | 190 | 210 |
| Total rec. protein yield [g] | 8.9 (16.55*) | 50.6 | 60.3 |
| Volumetric protein yield (titer) [g/L] | 0.92 (1.48*) | 4.5 | 5.4 |

Example 7

Figure 15:
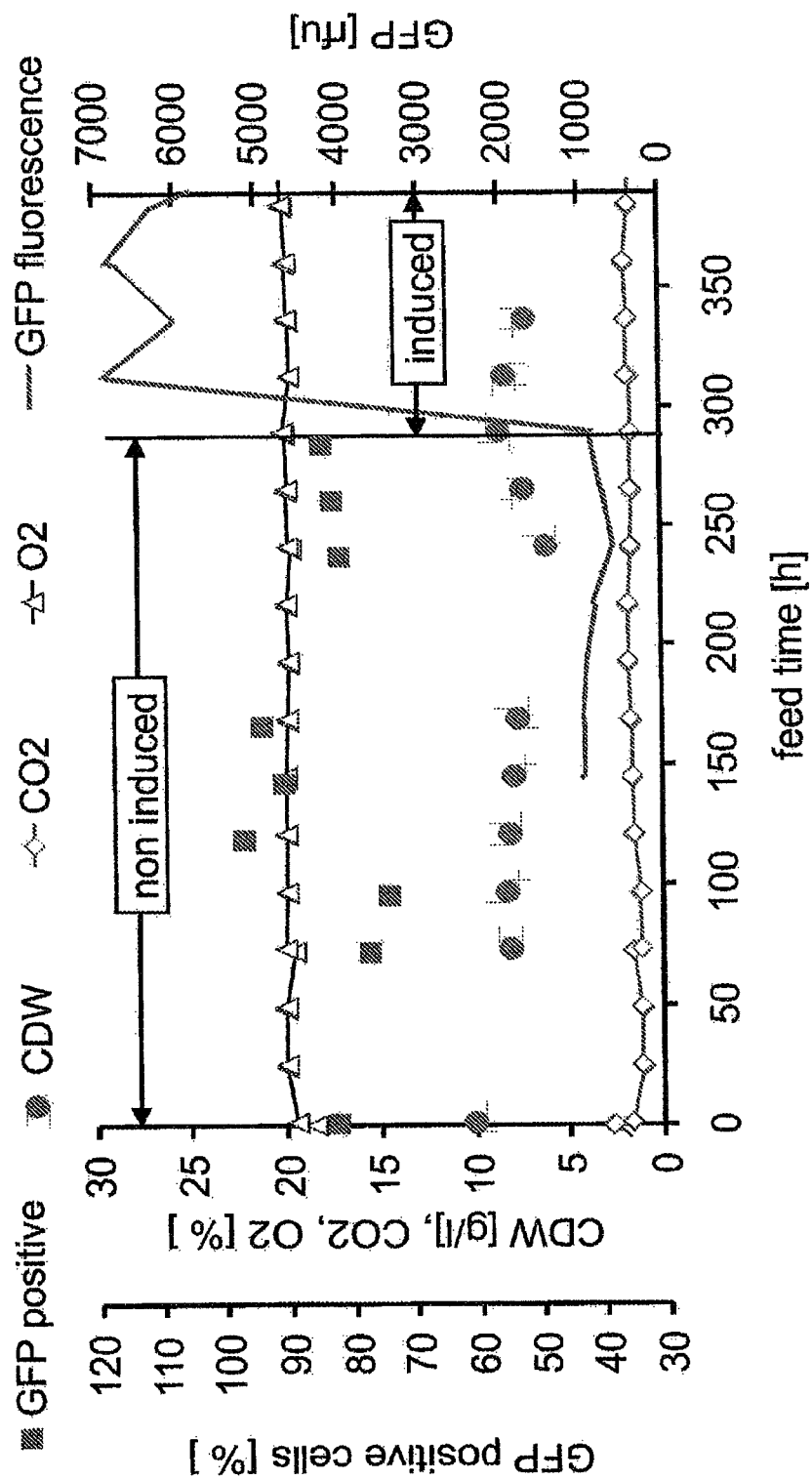
FIG. 15: Expression of soluble GFPmut3.1 with *E. coli* HMS174(DE3) in the continuous mode (chemostat) (ES6).

Expression of Soluble GFPmut3.1 with *E. coli* HMS174 (DE3) in the Continuous (Chemostat) Mode In order to verify the genetic stability of a genome-based (i.e. plasmid-free) expression system, a continuous cultivation experiment (chemostat) is conducted with the expression system ES6. A dilution rate of 0.1 $h^{-1}$ and a cell density of 10 g BDM per liter are set and the defined medium according to Example 2 is used for the main culture. The result of this cultivation is shown in FIG. 15. In the first part of the experiment the cells are grown in a non-induced state. The non-induced state of the main culture is maintained for more than 42 doublings without any detectable changes in the behavior of the subcultures. The fraction of producing cells is kept more or less constant between 75 to 95% (squares FIG. 15). Subsequently, close to 300 hours of feeding, the culture is fully induced with IPTG and about hours past induction the online fluorescence approximates the maximal level obtainable in this experimental setup. According to Reischer et al (2004) the specific cellular content of GFP is calculated to be approximately 140 to 170 mg GFP per g BDM. The cells are maintained in this induced state for more than 13.5 doublings. The course of the online fluorescence during this period shows rfu range between 6000 and 7000 units. These results show that the system stability of the genome based expression host is very high even for prolonged generations in the induced state. In contrast to plasmid-based systems, very high expression rates can be maintained with the systems based on genome integration which represents a clear benefit for the development of continuous manufacturing processes.

Example 8

Improved Induction Control by Pre-Defining Inducer Concentration

Tight induction control of recombinant gene expression is a very important aspect in bioprocessing. Contrary to plasmid-based pET/T7 systems with their high and varying gene dosage (plasmid copy number), the genome-based (plasmid free) T7 system used in the method of the invention strictly features a defined number of gene copies (one ore more) of the target gene. Due to this fact, the expression rate of genome based systems can be controlled more efficient. To demonstrate this benefit, a series of fed-batch cultivations with ES10 applying different induction levels (i.e. inducer concentrations) is conducted. Induction is performed by a single bolus of IPTG into the bioreactor to set an initial ratio of inducer per cell dry weight (CDW), followed by continuously feeding of IPTG to keep a defined concentration at a constant level. The ratios of IPTG to CDW are as follows: 0.5, 0.75, 1.0, 2.0 μmol gCDW$^{-1}$, up to a level of 20 μmol gCDW$^{1}$ which certainly results in a full titration of lac-repressor molecules (i.e. in the highest possible induction level). The off-line measured specific cellular fluorescence (spec. F) which is strongly correlated to the specific content of GFP (Reischer et. al 2004) is used to monitor product accumulation during induction and to calculate the specific product formation rate ($qP_F$) as follows:

$$qP_F = \frac{(spec.\ F_2 - spec.\ F_1)}{\left(\frac{CDW_1 + CDW_2}{2}\right) * (t_2 - t_1)}$$

Figure 16:
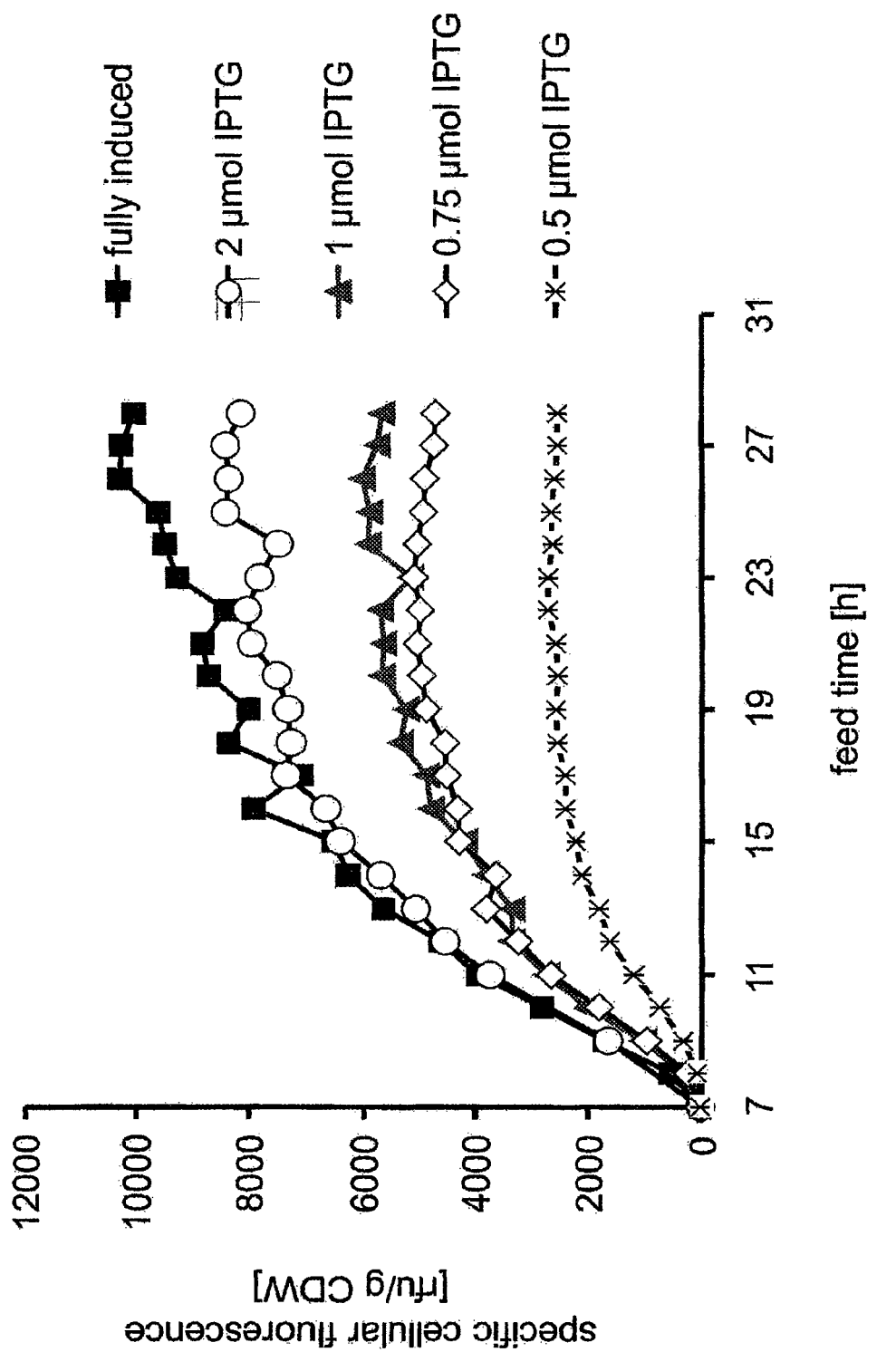
FIG. 16: Fed-batch cultivation employing genome-encoded expression system BL21 (DE3) in combination with controlled inductor dosage for production of the soluble GFPmut3.1.
Figure 17:
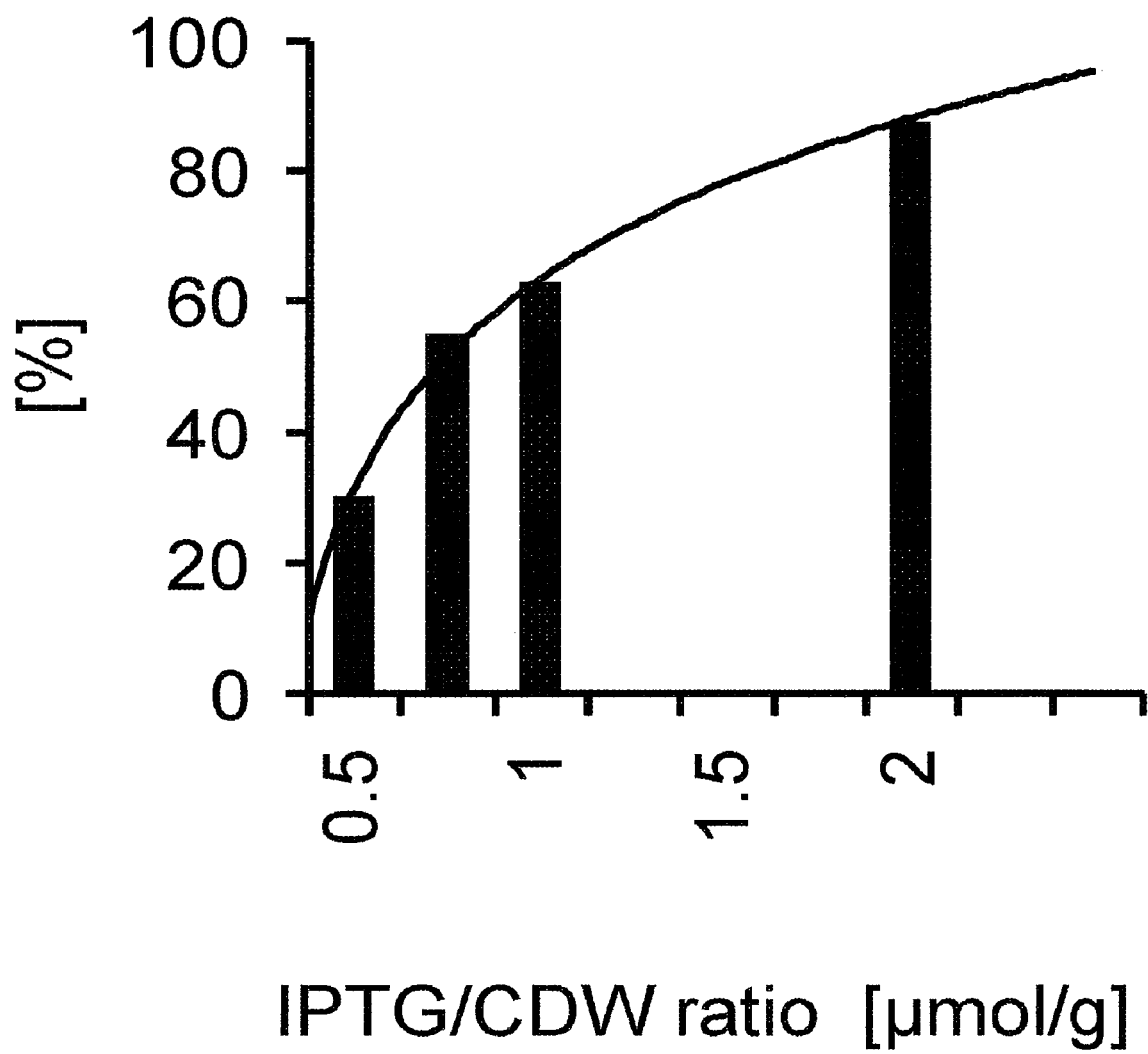
FIG. 17: Standardized average product formation rate (qP) of soluble GFPmut3.1 obtained from fed-batch cultivation employing genome-encoded expression system BL21 (DE3), in correlation with the concentration of inductor.

The applied range of IPTG to CDW ratios results in cellular fluorescence levels from 2000 to 10000 rfu's $g^{-1}$CDW at the end of the process which impressively proves the efficiency of the transcription tuning strategy (FIG. 16). The $qP_F$ of the fully induced system (20 μmol IPTG/gCDW) is fixed as maximum level of 100% and the average $qP_F$ values obtained in the experiments with limited induction are strongly correlated with the induction level (inducer concentration) following a logarithmic trend (FIG. 17 shows the standardized pP). These results imply that low level induction is more sensitive to changes in the IPTG/CDW ratio and requires tightly controlled inducer feed regimes based on real time estimated CDW. Furthermore the IPTG/CDW ratio which is required for full induction of the system can be estimated by extrapolation of the trend in FIG. 17 and will range between 3-5 μmol $g^{-1}$, which is substantially lower than the 20 μmol $g^{-1}$ used in the experiment. Each applied IPTG/CDW ratio results in a corresponding $qP_F$ level with a certain band-width, as follows:

|  | Induction level (IPTG concentration in μmol/gCDW) | | | |
| --- | --- | --- | --- | --- |
|  | 0.5 | 0.75 | 1 | 2 |
| Maximum level of specific product formation rate $qP_F$ (rfu/gh) | 500 | 800 | 1000 | 1200 |

As a conclusion, this example shows that a method based on genome-based expression according to the invention enables a better controllability of product yield and product formation rate.

REFERENCES

Andersen, D. C. and Reilly D. E. 2004. Production Technologies for Monoclonal Antibodies and their Fragments. Current Opinion in Biotechnology 2004, 15:456-462.

Baba T, Ara T, Hasegawa M, Takai Y, Okumura Y, Baba M, Datsenko K A, Tomita M, Wanner B L, Mori H., Construction of *Escherichia coli* K-12 in-frame, single-gene knockout mutants: the Keio collection. Mol Syst Biol. 2006; 2:2006. 0008. Epub 2006 Feb. 21.

Baneyx, F. (1999). Recombinant protein expression in *Escherichia coli*. Current Opinion in Biotechnology, 10; 411-421.

Bayer K, Jungbauer A, Kramer W, Lettner H, SchoÈnhofer W, Skias M, Steindl F, Taferner N, Uhl K (1990) Humane re-kombinante Superoxiddismutase. BioEngineering 6: 24±30.

Bentley, W. E.; Mirjalili, N.; Andersen, D. C.; Davis, R. H.; Kompala, D. S. Plasmid encoded protein: the principal factor in the "metabolic burden" associated with recombinant bacteria. Biotechnol. Bioeng. 1990, 35, 668-681.

Cashel M. The control of ribonucleic acid synthesis in *Escherichia coli*. IV. Relevance of unusual phosphorylated compounds from amino acid starved stringent strains. J Biol Chem. 1969; 244:3133-3141.

Chamberlin et al., New RNA polymerase from *Escherichia coli* infected with bacteriophage T7. Nature, 1970, 228: 227-231.

Choi, J. H. and Lee, S. Y. Secretory and extracellular production of recombinant proteins using *Escherichia coli*. Appl Microbiol Biotechnol. 2004 64(5): 625-635.

Cormack, B. P., Valdivia, R. H., Falkow, S. "FACS-optimised mutants of the green fluorescent protein (GFP)" Gene, 1996, 173(1): 33-8.

Craig, N. L: Transposon TN7. In Berg, D. E and Howe, M. H. (Eds.), Mobile DNA. American Society of Microbiology, Washington D.C., 1989, 211-225.

Cserjan-Puschmann, M.; Kramer, W.; Dürrschmid, E.; Striedner, G.; Bayer, K. Metabolic approaches for the optimisation of recombinant fermentation processes. Appl. Microbiol. Biotechnol, 1999, 53, 43-50.

Datsenko K. A., and Wanner B. L. One-step inactivation of chromosomal genes in *Escherichia coli* K-12 using PCR products. Proc. Nat. Acad. Sciences U.S.A, 2000, 97, 6640-6645.

Diaz-Rizzi, J. D. and Hernandez, M. E. (2000). Plasmid effects on *Escherichia coli* metabolism. Crit Rev Biotechn 20:2, 79-108.

Gerdes S. Y., Scholle M. D., D'Souza M., Bernal A., Baev M. V., Farrell M., Kurnasov O. V., Daugherty M. D., Mseeh F., Polanuyer B. M., Campbell J. W., Anantha S., Shatalin K. Y., Chowdhury S. A. K., Fonstein M. Y., Osterman A. L. From genetic footprinting to antimicrobial drug targets: Examples in cofactor biosynthetic pathways. Journal of Bacteriology, August 2002, Vol. 184, No. 16, pp 4555-4572.

Gerdes S Y, Scholle M D, Campbell J W, Balazsi G, Ravasz E, Daugherty M D, Somera A L, Kyrpides N C, Anderson I, Gelfand M S, Bhattacharya A, Kapatral V, D'Souza M, Baev M V, Grechkin Y, Mseeh F, Fonstein M Y, Overbeek R, Barabasi A L, Oltvai Z N, Osterman A L. Experimental determination and system level analysis of essential genes in *Escherichia coli* MG1655. J Bacteriol. 2003, 185, 5673-84.

Glick, B. R. Metabolic load and heterologous gene expression.
Biotechnol. Adv. 1995, 13, 247-261.

Grabherr R., Nilsson E., Striedner G., Bayer K. Stabilizing plasmid copy number to improve recombinant protein production. Biotechnology and Bioengineering, 2002, 75: 142-147.

Guzman L M, Belin D, Carson M J, Beckwith J. Tight regulation, modulation, and high-level expression by vectors containing the arabinose PBAD promoter. J Bacteriol., 1995, July 177(14):4121-30.

Hannig, G., and Makrides, S. C. Strategies for optimizing heterologous protein expression in *Escherichia coli*. Trends in Biotechnology, 1998, 16, 54-60.

Herring C D, Raghunathan A, Honisch C, Patel T, Applebee M K, Joyce A R, Albert T J, Blattner F R, van den Boom D, Cantor C R, Palsson B O. Comparative genome sequencing of *Escherichia coli* allows observation of bacterial evolution on a laboratory timescale. Nat Genet. 2006, December 38(12):1406-1412, Epub 2006 Nov. 5.

Hoffman, B. J.; Broadwater, J. A.; Johnson, P.; Harper, J.; Fox, B. G.; Kenealy, W. R. Lactose fed-batch overexpression of recombinant metalloproteins in *Escherichia coli* BL21(DE3): process control yielding high levels of metal-incorporated, soluble protein. Protein Expression Purif. 1995, 6, 646-654.

Holliger, P. and Hudson, P. J. Engineered antibody fragments and the rise of single domains. Nature Biotechnology, 2005, 23/9, 1126-36.

Jahic M, F. Wållberg, M. Bollok, P. Garcia and S-O Enfors, 2003. Use of a temperature limited fed-batch technique to control proteolysis in *Pichia pastoris* bioreactor cultures. Micriobial Cell Factories, 2003.

Jain, C. (2006). Overexpression and purification of tagged *Escherichia coli* proteins using a chromosomal knock-in strategy. Protein Expr Purif.; 46:2; 294-298.

Jeong, K. J., Choi, J. H., Yoo, W. M., Keum, K. C., Yoo, N. C., Lee, S. Y. and Sung, M. H. Constitutive production of human leptin by fed-batch culture of recombinant rpoS *Escherichia coli*. Protein Expression and Purification, 2004, 36, 150-156.

Kleman, G. L., Chalmers, J. J., Luli, G. W. and Strohl, W. R. A predictive and feedback control algorithm maintains a constant glucose concentration in fed-batch fermentations. Appl Environ Microbiol. 57(4), 1991, 910-917.

Lee, S. Y. High cell-density culture of *Escherichia coli*. Trends in Biotechnology, 1996, 14, 98-105.

Lennox E. S. Transduction of linked genetic characters of the host by bacteriophage P1. Virology 1955 July; 1(2) 190-206.

Makrides, S. C. Strategies for Achieving High-Level Expression of Genes in *Escherichia coli*. Microbiological Reviews, 1996, 60/3, 512-538.

Martinez-Morales, F., Borges, A. C., Martinez, A., Shanmugam, K. T. and Ingram, L. O. (1999). Chromosomal Integration of Heterologous DNA in *Escherichia coli* with Prescise Removal of Markers and Replicons Used during Construction. Journal of Bacteriology, 181:22; 7143-7148.

Mau B, Glasner J D, Darling A E, Perna N T. Genome-wide detection and analysis of homologous recombination among sequenced strains of *Escherichia coli*. Genome Biol. 2006; 7(5):R44. Epub 2006 May 31.

Mierau, I., Peter Leij, P., van Swam, I., Blommestein, B., Floris, E., Mond, J. and Smid, E. J. Industrial-scale production and purification of a heterologous protein in *Lactococcus lactis* using the nisin-controlled gene expression system NICE: The case of lysostaphin. Microbial Cell Factories, 2005, 4:15 doi:10.1186/1475-2859-4-15.

Murphy, K. C. (1998). Use of Bacteriophage λ Recombination Functions To Promote Gene Replacement in *Escherichia coli*. Journal of Bacteriology; 180:8; 2063-2071.

Muyrers, J. P. P., Zhang, Y. and Stewart A. F, ET-cloning: think recombinant first. Genet Eng (NY), 2000, 22:77-98.

Muyrers, J. P. P., Zhang, Y. and Stewart A. F. Introducing Red/ET Recombination: DNA Engineering for the $21^{st}$ Century. Gene Cloning & Expression Technologies; 2002, edited by Michael P. Weiner & Quinn Lu, Biotechniques PRESS '02.

Oakley J L., and Coleman J E., Structure of a promoter for T7 RNA polymerase. Proc Natl Acad Sci USA, 1977, October 74(10):4266-70.

Ochem, A. E, Skopac, D., Costa, M., Rabilloud, T., Vuillard, L., Simoncsits, A., Giacca, M. and Falaschi, A. Functional Properties of the Separate Subunits of Human DNA Helicase II/Ku Autoantigen. Journal of Biological Chemistry; 1997, Vol 272/47, 29919-29926.

Olson, P., Zhang, Y., Olsen, D., Owens, A., Cohen, P., Nguyen, K., Ye, J. J., Bass, S., and Mascarenhas, D. (1998) High-Level Expression of Eukaryotic Polypeptides from Bacterial Chromosomes. Protein Expression and Purification; 14, 160-166.

Panayotatos and Wells, Recognition and initiation site for four late promoters of phage T7 is a 22-base pair DNA sequence. Nature, 1979, Jul. 5, 280:35-39.

Pfaffenzeller, I., Mairhofer, J., Striedner, G., Bayer, K. and Grabherr, R. (2006). Using ColE1-derived RNA I for suppression of a bacterially encoded gene: implication for a novel plasmid addiction system. Biotechnol. J. 2006, 1, 675-681.

Phillips, G. J. New cloning vectors with temperature-sensitive replication. Plasmid, 1998, 41, 78-81.

Pósfai, G., et al., In vivo excision and amplification of large segments of the *Escherichia coli* genome. Nucleic Acids Res., 1994, Jun. 25; 22(12):2392-8.

Poo, H., Song, J. J., Hong, S. P., Choi, Y. H., Yun, S. W., Kim, J. H., Lee, S. C., Lee, S. G. and Sung, M. H. Novel high-level constitutive expression system, pHCE vector, for a convenient and cost-effective soluble production of human tumor necrosis factor-α. Biotechnology Letters, 2002, 24, 1185-1189.

Reischer, H., I. Schotola, et al. Evaluation of the GFP signal and its aptitude for novel on-line monitoring strategies of recombinant cultivation processes. Journal of Biotechnology, 2004, 108(2): 115-125.

Remmert, K., Vullhorst, D. and Hinssen, H. In Vitro Refolding of Heterodimeric CapZ Expressed in *E. coli* as Inclusion Body Protein. Protein Expression and Purification, 2000, Vol. 18/1, 11-19.

Retallack, D. M., Thomas, T. C., Shao, Y., Haney, K. L., Resnick, S. M., Lee, V. D. and Squires, C. H. Identification of anthranilate and benzoate metabolic operons of *Pseudomonas fluorescens* and functional characterization of their promoter regions. Microbial Cell Factories, 2006, 5:1 doi:10.1186/1475-2859-5-1.

Rogers, M., Ekaterinaki, N., Nimmo, E., Sherratt, D., Analysis of Tn7 transposition. Mol Gen Genet, 1986, December 205:3 550-6.

Sheffield, P. J., McMullen, T. W. P., Li, J., Ho, Y. S., Garrard, S. M., Derewenda, U. and Derewenda, Z. S. Preparation and crystal structure of the recombinant $\alpha_1/\alpha_2$ catalytic heterodimer of bovine brain platelet-activating factor acetylhydrolase Ib. Protein Engineering, 2001, Vol 14/7, 513-519.

Shimomura, O., Johnson, F. H., Saiga, Y. "Extraction, purification and properties of Aequorin, a bioluminescent protein from luminous hydromedusan, *Aequorea*." J Cell Comp Physiol, 1962, 59: 223-239.

Squires, C. H., Retallack, D. M., Chew, L. C., Ramseier, T. M., Schneider, J. C., Talbot, H. W. Heterologous Protein Production in *P. fluorescens*.
BioProcesss International, December 2004, 54-58.

Stark R., Meyers G., Rümenapf T., Thiel H.-J. J. Virol. 1993, 67, 7088-7095.

Sternberg N and Hoess R. The molecular genetics of bacteriophage P1.
Annu Rev Genet 1983; 17 123-54.

Striedner G, Cserjan-Puschmann M, Potschcher F, Bayer K. Tuning the transcription rate of recombinant protein in strong *Escherichia coli* expression systems through repressor titration. Biotechnol Prog. 2003, Sep.-Oct. 19(5):1427-1432.

Studier, F. W., and Moffatt, B. A. Use of the bacteriophage T7 RNA polymerase to direct selective high-level expression of cloned genes. J. Mol. Biol., 1986, 189, 113-130.

Studier, F. W.; Rosenberg, A. L.; Dunn, J. J.; Dubendorff, J. W. Use of T7 RNA polymerase to direct expression of cloned genes. Meth. Enzym., 1990, 185, 60-89.

Summers, D. K. The kinetics of plasmid loss. Tibtech 1991, Vol 9, 273-278.

Teich, A.; Lin, H. Y.; Andersson, L.; Meyer, S.; Neubauer, P. Amplification of ColE1 related plasmids in recombinant cultures of *Escherichia coli* after IPTG induction. J. Biotechnol. 1998, 64, 197-210.

Thiel H.-J., Stark R., Weiland E., Rümenapf T., Meyers G. J. Virol. 1991, 65, 4705-4712

Tsao, K. L. and Waugh, D. S. Balancing the production of two recombinant proteins in *Escherichia coli* by manipulating plasmid copy number: high-level expression of heterodimeric Ras farnesyltransferase. Protein Expression and Purification, 1997, Vol 11/3, 233-40.

Vetcher L; Tian Z Q, McDaniel R, Rascher A, Revill W P, Hutchinson C R, Hu Z. Rapid engineering of the geldanamycin biosynthesis pathway by Red/ET recombination and gene complementation. Appl Environ Microbiol. 2005, April 71(4):1829-35.

Waddell, C. S. and Craig, N. L. Tn7 transposition: two transposition pathways directed by five Tn7-encoded genes. Genes Dev, 1988, Feb. 2:2, 137-49.

Wenzel S C, Gross F, Zhang Y, Fu J, Stewart A F, Muller R. Heterologous expression of a myxobacterial natural products assembly line in pseudomonads via red/ET recombineering. Chem Biol. 2005, 12(3): 349-356.

Wilson, K. and Walker, J. (2005). Principles and Techniques of Biochemistry and Molecular Biology. $6^{th}$ Ed., Cambridge University Press.

Wiskerchen M., Belzer S. K., Collett M. S. J. Virol. 1991, 65, 4508-4514.

Wróbel, B., and Wegrzyn, G. Replication regulation of ColE1-like plasmids in amino acid-starved *Escherichia coli*. Plasmid 1998, 39, 48-62.

Yu, D., Ellis, H., Lee, C., Jenkins, N., Copeland, N., Court, D. An efficient recombination system for chromosome engineering in *Escherichia coli*. PNAS. 2000, May 23, Vol. 987, No. 11, 5978-5983.

Zhang, Y., Buchholz, F., Muyrers, J. P. P. and Stewart, A. F. (1998). A New Logic for DNA Engineering Using Recombination in *Escherichia coli*. Nature Genetics; 20:2, 123-128.

Zhou, L., Zhang, K. and Wanner B. L. (2004). Chromosomal expression of foreign and native genes from regulatable promoters in *Escherichia coli*.
Methods Mol. Biol. 2004, 267:123-34.

U.S. Pat. No. 4,680,262
U.S. Pat. No. 4,952,496
U.S. Pat. No. 4,963,495
US 2006/0003404
WO 1996/40722
WO 2001/18222
WO 2003/050240
WO 2006/029985
WO 2006/113959

The invention claimed is:

1. A method for plasmid-free production of a heterologous protein of interest, comprising the steps of
   a) cultivating bacterial expression host cells in a culture medium, said cultivating comprising a mode that employs adding a feeding medium, wherein said mode is selected from fed-batch mode, semi-continuous mode, and continuous mode, wherein
      (i) one copy of a DNA construct is integrated in the chromosome of the host cells, and wherein said DNA construct consists essentially of a DNA sequence encoding the heterologous protein of interest under the control of a promoter that enables expression of the heterologous protein from the integrated one copy of the DNA construct, a ribosome binding site, two terminally flanking regions homologous to a genomic region of the host cells that enable homologous recombination, and optionally one or more components useful for expression of the heterologous protein,
      or
      (ii) one copy of a DNA construct is integrated in the chromosome of the host cells, and wherein said DNA construct consists essentially of two copies of a DNA sequence encoding the heterologous protein of interest, wherein each copy of said DNA sequence encoding the heterologous protein of interest is under the control of its own promoter that enables expression of the heterologous protein from the integrated one cop of the DNA construct or the two copies of the DNA sequence encoding the heterologous protein of interest are under the control of one promoter, ribosome binding sites operationally linked to each of the two copies of the DNA sequence encoding the heterologous protein of interest two terminally flanking regions homologous to a genomic region of the host cells that enable homologous recombination, and optionally one or more components useful for expression of the heterologous protein, or (iii) one copy of a first DNA construct and one copy of a second DNA construct are integrated in the chromosome of the host cells, and wherein each DNA construct consists essentially of a DNA sequence encoding the heterologous protein of interest under the control of a promoter that enables expression of the heterologous protein from the integrated DNA construct, a ribosome binding site, two terminally flanking regions homologous to a genomic region of the host cells that enable homologous recombination, and optionally one or more components useful for expression of the heterologous protein, and wherein the two terminally flanking regions homologous to a genomic re ion for the first DNA construct and the second DNA construct can be the same or different, and wherein the one copy of the DNA construct of (i) or (ii) or the one copy of the first DNA construction and the copy of the second DNA construct of (iii) are maintained in the chromosome of the cultivated expression host cells, and wherein the host cells do not contain any DNA construct encoding the heterologous protein of interest that is present in a plasmid, and wherein cultivating takes place under conditions where the heterologous protein of interest is expressed;

b) harvesting the heterologous protein of interest expressed by the expression host cells; and c) isolating and purifying the heterologous protein of interest on a manufacturing scale in a bioreactor with a minimum volume of 5 liter.

2. The method of claim 1, wherein said promoter is an inducible promoter.

3. The method of claim 2, wherein said inducible promoter is selected from the group consisting of the tac promoter, the trc promoter, the lac promoter, the lacUV5 promoter, the trp promoter, the lambda promoter pL, the phoA promoter, the T3 promoter, the T5 promoter, and the araBAD promoter.

4. The method of claim 2, wherein said promoter is a leaky promoter.

5. The method of claim 2, wherein the expression of said protein of interest is induced by the presence of an inductor.

6. The method of claim 5, wherein the inductor is added in a continuous manner.

7. The method of claim 6, wherein the inductor is added at a concentration that is proportional to the biomass, resulting in a constant ratio of inductor to biomass.

8. The method of claim 5, wherein the promoter is selected from the group consisting of the T7 promoter, the tac promoter, the trc promoter, the lac promoter, the lacUV5 promoter, the T3 promoter, and the T5 promoter, and wherein the inductor is IPTG.

9. The method of claim 8, wherein the concentration of IPTG in the culture medium is in a range of 0.1-30 µg per g cell dry weight.

10. The method of claim 9, wherein said range is 0.5-20 µg per g cell dry weight.

11. The method of claim 5, wherein the promoter is selected from the group consisting of the T7 promoter, the tac promoter, the trc promoter, the lac promoter, the lacUV5 promoter, the T3 promoter, and the T5 promoter, and wherein the inductor is lactose.

12. The method of claim 5, wherein the inductor is present in the batch phase from the beginning of the cultivation.

13. The method of claim 1, wherein said bacterial expression host cells are *E. coli* cells.

14. The method of claim 13, wherein said *E. coli* expression host cells contain a T7 RNA polymerase gene in their genome and wherein said promoter is the T7 promoter.

15. The method of claim 14, wherein said *E. coli* expression host cells have been obtained by integrating the one copy of the DNA construct of (i) or (ii) or the one copy of the first DNA construction and the copy of the second DNA construct of (iii) into *E. coli* host cells that already innately contain the T7 RNA polymerase gene in their genome.

16. The method of claim 15, wherein said *E. coli* host cells that already innately contain the T7 RNA polymerase gene in their genome are selected from the strains BL21(DE3), HMS174(DE3) or their derivatives.

17. The method of claim 15, wherein said *E. coli* host cells containing the T7 RNA polymerase gene in their genome are non-lysogenic.

18. The method of claim 14, wherein said *E. coli* expression host cells have been obtained by integrating into *E. coli* host cells that do not contain the T7 RNA polymerase gene in their genome, a DNA construct that carries, as an additional element, a T7 RNA polymerase gene.

19. The method of claim 1, wherein said promoter is a constitutive promoter.

20. The method of claim 19, wherein said promoter is a HCD promoter.

21. The method of claim 1, wherein said expression host cells contain the one copy of the DNA construct of (i) or (ii) or the one copy of the first DNA construction and the copy of the second DNA construct of (iii) integrated at an attachment site.

22. The method of claim 21, wherein said attachment site is the attTn7 site.

23. The method of claim 1, wherein said expression host cells contain the one copy of the DNA construct of (i) or (ii) or the one copy of the first DNA construction and the copy of the second DNA construct of (iii) integrated at the site of a DNA marker sequence that is contained in the genome of the bacterial host cell.

24. The method of claim 23, wherein said marker DNA sequence encodes a protein that provides antibiotic resistance.

25. The method of claim 23, wherein said marker DNA sequence encodes a fluorescent protein.

26. The method of claim 1, wherein the one copy of the DNA construct of (i) or (ii) or the one copy of the first DNA construction and the copy of the second DNA construct of (iii) contains, as one component useful for expression of the heterologous protein, a marker sequence encoding a marker protein.

27. The method of claim 26, wherein said marker protein is a protein which complements an auxotrophic mutation of the bacterial host cell, thereby rendering the expression host cell prototrophic.

28. The method of claim 26, wherein said marker DNA sequence encodes a protein that confers an antibiotic resistance.

29. The method of claim 26, wherein said marker DNA sequence encodes a fluorescent protein.

30. The method of claim 1, wherein cultivation is in the fed-batch mode with a predefined feeding mode.

31. The method of claim 30, wherein the predefined feeding mode is performed according to an exponential function.

32. The method of claim 1, wherein cultivation is in the fed-batch mode with a feedback-controlled feeding mode.

33. The method of claim 32, wherein the heterologous protein of interest is secreted from the cytoplasm into the periplasm and/or culture medium.

34. The method of claim 1, wherein the heterologous protein of interest is a heterodimer and wherein the DNA molecules encoding the two monomers are present on the same or on different DNA constructs.

35. The method of claim 34, wherein the protein is secreted from the cytoplasm into the periplasm and/or culture medium.

36. The method of claim 1 wherein the one copy of the DNA construct of (i) or (ii), the one copy of the first DNA construction of (iii), or the copy of the second DNA construct of (iii) comprises one or more components selected from the group consisting of a regulator gene (including parts for gene regulation), an initially transcribed sequence (ITS), a transcription terminating DNA sequence, sequences coding for antibiotic selection markers, prototrophic selection markers or fluorescent markers, genes coding for metabolic markers, genes that improve protein expression, and flippase recognition target sites.

* * * * *

UNITED STATES PATENT AND TRADEMARK OFFICE
CERTIFICATE OF CORRECTION

PATENT NO. : 10,752,930 B2
APPLICATION NO. : 15/594249
DATED : August 25, 2020
INVENTOR(S) : Gerald Striedner et al.

Page 1 of 1

It is certified that error appears in the above-identified patent and that said Letters Patent is hereby corrected as shown below:

In the Claims

Column 31, Claim 1, Line 28:
"genomic re ion for the" should read: --genomic region for the--.

Signed and Sealed this
Fifteenth Day of December, 2020

Andrei Iancu
*Director of the United States Patent and Trademark Office*